US008652796B2

(12) United States Patent (10) Patent No.: US 8,652,796 B2
Nibert et al. (45) Date of Patent: Feb. 18, 2014

(54) METHOD AND COMPOSITION FOR DETECTING PROTEIN-PROTEIN AND PROTEIN-NUCLEIC ACID INTERACTIONS

(75) Inventors: Max L. Nibert, Roslindale, MA (US); Cathy Lea Miller, Brookline, MA (US); Teresa J. Broering, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1369 days.

(21) Appl. No.: 11/856,099

(22) Filed: Sep. 17, 2007

(65) Prior Publication Data

US 2008/0153111 A1 Jun. 26, 2008

Related U.S. Application Data

(63) Continuation of application No. PCT/US2006/009319, filed on Mar. 15, 2006.

(60) Provisional application No. 60/674,119, filed on Apr. 22, 2005, provisional application No. 60/661,827, filed on Mar. 15, 2005.

(51) Int. Cl.
*C12Q 1/70* (2006.01)
(52) U.S. Cl.
USPC .............. 435/29; 435/7.8; 435/235.1; 506/43
(58) Field of Classification Search
None
See application file for complete search history.

(56) References Cited

PUBLICATIONS

Ali and DeCaprio, "Cellular transformation by SV40 Large T antigen . . . ," *Seminars in Cancer Biol.*, 11:15-22 (2001).
Antczak and Joklik, "Reovirus Genome Segment Assortment into Progeny Genomes . . . ," *Virology*, 187:760-776 (1992).
Attoui et al., "Common evolutionary origin of aquareoviruses and orthoreoviruses revealed by genome characterization . . . ," *J. Gen. Virol.*, 83:1941-1951 (2002).
Becker et al., "Reovirus σNS Protein Is Required for Nucleation of Viral Assembly Complexes . . . ," *J. Virol.* 75:1459-1475 (2001).
Becker et al., "Reovirus σNS and μNS Proteins Form Cytoplasmic Inclusion Structures in the Absence of Viral Infection," *J. Virol.*, 77(10):5948-5963 (2003).
Beneviste et al., "Characterization of Internalization and Endosome Formation of Epidermal Growth Factor in Transfected NIH-3T3 Cells by computerized Image-Intensified Three-Dimensional Fluorescence Microscopy," *J. Cell Biol.*, 109:2105-2115 (1989).
Broering et al., "Reovirus Nonstructural Protein μNS Binds to Core Particles but Does Not Inhibit their Transcription and Capping Activities," *J. Virol.*, 74(12):5516-5524 (2000).
Broering et al., "Mammalian Reovirus Nonstructural Protein μNS Forms Large Inclusions and Colocalizes with Reovirus Microtubule-Associated Protein μ2 in Transfected Cells," *J. Virol.*, 76(16):8285-8297 (2002).

Broering et al., "Reovirus Nonstructural Protein μNS Recruits Viral Core Surface Proteins . . . ," *J. Virol.*, 78(4):1882-1892 (2004).
Broering et al., "Carboxyl-Proximal Regions of Reovirus Nonstructural Protein μNS necessary and Sufficient for Forming Factory-Like Inclusions," *J. Virol.*, 79(10): 6194-6206 (2005).
Brookes et al., "Characterization of virus inclusion bodies in bluetongue virus-infected cells," *J. Gen. Virol.*, 74:525-530 (1993).
Campbell et al., "A monomeric red fluorescent protein," *Proc. Natl. Acad. Sci. USA*, 99(12):7877-7882 (2002).
Collot-Teieira et al., "Human tumor suppressor p53 and DNA viruses," *Rev. Med. Virol.* 14:301-319 (2004).
Dales, "Association Between the Spindle Apparatus and Reovirus," *Proc. National. Acad. Sci. USA*, 50:268-275 (1963).
Dales and Gomatos, "The Uptake and Development of Reovirus in Strain L Cells Followed with Labeled Viral Ribonucleic Acid and Ferritin-Antibody Conjugates," *Virology* 25:193-211 (1965).
Eichwald et al., "Characterization of rotavirus NSP2/NSP5 interactions and the dynamics of viroplasm formation," *J. Gen. Virol.*, 85:625-634 (2004).
Fields et al., "Temperature-Sensitive Mutants of Reovirus Type 3 . . . ," *Virology*, 43:569-578 (1971).
Fujimuro et al., "Production and characterization of monoclonal antibodies specific to multi-ubiquitin chains of polyubiquitinated proteins," *FEBS Letts*. 349:173-189 (1994).
Gillian et al., "Amino Terminus of Reovirus Nonstructional Protein σNS Is Important for ssRNA Binding and Nucleoprotein Complex Formation," *Virology* 240:1-11 (1998).
Gillian et al., "Reovirus Protein σNS Binds in Multiple Copies to Single-Stranded RNA and Shares Properties with Single-Stranded DNA Binding Proteins," *J. Virol*. 74:5939-5948 (2000).
Gomatos et al., "Small Reovirus Particles Composed Solely of Sigma NS with Specificity for Binding Different Nucleic Acids," *J. Virol.*, 39(1):115-124 (1981).
Hayes et al., "The Interaction of a Series of Hybridoma IgGs with Reovirus Particles Demonstration that the Core Protein λ2 Is Exposed on the Particle Surface," Virology, 108:147-155 (1981).
Hopfner et al., "The Rad50 zinc-hook is a structure joining Mre11 complexes in DNA recombination and repair," *Nature*, 418:562-566 (2002).
Huismans and Joklik, "Reovirus-Coded Polypeptides in Infected Cells: Isolation of Two Native Monomeric Polypeptides with Affinity for Sing-Stranded and Double-Stranded RNA . . . ," *Virology*, 70:411-424 (1976).
Huse et al., "A $Zn^2$ Ion Links the Cytoplasmic Tail of CD4 and the N-terminal Region of Lek," *J. Biol. Chem*. 273(30):18729-18733 (1998).
Kim et al., "Bidirectional Transmembrane Signalling by Cytoplasmic Domain Separation in Integrins," *Science*, 301:1720-1725 (2003).
Lee et al., "Characterization of Anti-Reovirus Immunoglobulins Secreted by Cloned Hybridoma Cell Lines," *Virology* 108:134-146 (1981).
Mayor, "Studies on Reovirus. III. A Labile, Single-Stranded Ribonucleic Acid Associated with the Late Stages of Infection," *J. NCI* 35:919-922 with plates on pp. 924 and 925 (1965).
Mbisa et al., "Reovirus μ2 Protein Determines Strain-Specific Differences in the rate of Viral Inclusion Formation in L929 Cells," *Virology* 272:16-26 (2000).

(Continued)

*Primary Examiner* — Christopher M Gross
(74) *Attorney, Agent, or Firm* — Banner & Witcoff, Ltd.

(57) ABSTRACT

The present invention provides methods and compositions for detecting protein-protein and/or protein-nucleic acid interactions in cells.

16 Claims, 12 Drawing Sheets

(56) References Cited

PUBLICATIONS

McCutcheon et al., "Mammalian Reovirus M3 Gene Sequences and Conservation of Coiled-Coil Motifs near the Carboxyl Terminus of the μNS Protein," *Virology*, 264:16-24 (1999).

Miller et al., "Flock House Virus RNA Replicates on Outer Mitochondrial Membranes in *Drosophila* Cells," *J. Virol.*, 75(23):11664-11676 (2001).

Miller et al., "Reovirus σNS Protein Localized to Inclusions through an Association Requiring the μNS Amino Terminus," *J. Virol.*, 77(8):4566-4576 (2003).

Mohan et al., "The N- and C-Terminal Regions or Rotavirus NSP5 Are the Critical Determinants for the Formation of Viroplasm-Like Structures Independent of NSP2," *J. Virol.*, 77:12184 12192 (2003).

Morgan and Zweerink, "Characterization of Transcriptase and Replicase Particles Isolated from Reovirus-Infected Cells," *Virology*, 68:455-466 (1975).

Moss, B. (2001) "*Poxviridae*: the viruses and their replication," 2849-2883. In D. M. Knipe and P. M. Howley (ed.), *Fields Virology*. Lippincott Williams & Wilkins, Philadelphia.

Parker et al., "Reovirus Core Protein μ2 Determines the Filamentous Morphology of Viral Inclusion Bodies by Interacting with and Stabilizing Microtubules," *J. Virol.*, 76(9):4483-4496 (2002).

Pipas et al., "Role of T antigen interactions with p53 in tumorigenesis," *Seminars in Cancer Biol.*, 11:23-30 (2001).

Quimby et al., "Nuclear transport mechanisms," *Cell. Mol. Life Sci.*, 58:1766-1773 (2001).

Restrepo-Hartwig and Ahlquist, "Brome Mosaic Virus Helicase- and Polymerase-Like Proteins Colocalize on the Endoplasmic Reticulum at Sites of Viral RNA Synthesis," *J. Virol.*, 70(12):8908-8916 (1996).

Rhim et al., "Cytochemical, Fluorescent-Antibody and Electron Microscopic Studies on the Growth of Reovirus (ECHO 10) in Tissue Culture," *Virology*, 17:342-355 (1962).

Richardson et al., "Synthesis in *Escherichia coli* of the Reovirus Nonstructional Protein σNS," *J. Virol.*, 56:527-533 (1985).

Roizman et al. (2001) "Herpes simplex viruses and their replication," pp. 2399-2459. In D. M. Knipe and P. M. Howley (ed.), *Fields Virology*. Lippincott Williams & Wilkins, Philadelphia.

Schwartz et al., "A Positive-Strand RNA Virus Replication Complex Parallels Form and Function of Retrovirus Capsids," *Mol. Cell*, 9:505-514 (2002).

Sharpe et al., "The Interaction of Mammalian Reoviruses with the Cytoskeleton of Monkey Kidney CV-1 Cells," *Virology*, 120:399-411 (1982).

Silverstein and Dales, "The Penetration of Reovirus RNA and Initiation of its Genetic Function in L-Strain Fibroblasts," *J. Cell Biol.*, 36(1):197-230 (1968).

Silverstein and Schur, "Immunofluorescent Localization of Double-Stranded RNA in Reovirus-Infected Cells," *Virology* 41:564-566 (1970).

Silvestri et al., "Rotavirus Replication: Plus-Sense Templates for Double-Stranded RNA Synthesis Are Made in Viroplasms," *J. Virol.* 78(14):7763-7774 (2004).

Spendlove et al., "Effect of Antimitotic Agents on Intracellular Reovirus Antigen," *Cancer Res.* 24:1826-1833 (1964).

Stamatos and Gomatos, "Binding to selected regions of reovirus mRNAs by a nonstructural reovirus protein," *Proc. Natl. Acad. Sci. USA*, 79:3457-3461 (1982).

Theron et al., "Site-specific mutations in the NS2 protein of epizootic haemorrhagic disease virus markedly affect the formation of the cytoplasmic inclusion bodies," *Arch. Virol.*, 141:1143-1151 (1996).

Touris-Otero et al., "Avian Reovirus Morphogenesis Occurs within Viral Factories and Begins with the Selective Recruitment of σNS and λA to μNS Inclusions," *J. Mol. Biol.* 341:361-374 (2004).

Touris-Otero et al., "Avian reovirus nonstructural protein μNS forms viroplasm-like inclusions and recruits protein σNS to these structures," *Virology*, 319:94-106 (2004).

Wiener et al., "The Sequence of Reovirus Serotype 3 Genome Segments M1 and M3 Encoding the Minor Protein μ2 and the Major Nonstructural Protein μNS, Respectively," *Virology*, 169:293-304 (1989).

Wilson et al., "The Structure of an Antigenic Determinant in a Protein," *Cell* 37:767-778 (1984).

Wolf et al., "MultiCoil: A program for predicting two-and three-stranded coiled coils," *Protein Sci.*, 6:1179-1189 (1997).

Zweerink et al., "Essential and Nonessential Noncapsid Reovirus Proteins," *Virology*, 45:716-723 (1971).

METHOD AND COMPOSITION FOR DETECTING PROTEIN-PROTEIN AND PROTEIN-NUCLEIC ACID INTERACTIONS

CROSS-REFERENCE OF RELATED U.S. APPLICATIONS

This application is a continuation of PCT application no. PCT/US2006/009319, designating the United States and filed Mar. 15, 2006; which claims the benefit of the filing date of U.S. provisional application Ser. No. 60/674,119, filed Apr. 22, 2005; and U.S. provisional patent application Ser. No. 60/661,827, filed Mar. 15, 2005; each of which is hereby incorporated herein by reference in its entirety.

STATEMENT OF GOVERNMENT INTERESTS

This invention was made with government support under National Institutes of Health grant number R01 AI47904. The Government has certain rights in the invention.

FIELD OF THE INVENTION

Embodiments of the present invention relate to detecting protein-protein and/or protein-nucleic acid interactions.

BACKGROUND

Viruses with ten-segmented, double-stranded (ds) RNA genomes from the family Reoviridae, genus *Orthoreovirus*, are believed to replicate in distinctive, cytoplasmic inclusion bodies (Broering (2002) *J. Virol.* 76:8285; Dales (1963) *Proc. Natl. Acad. Sci. USA* 50:268; Dales et al. (1965) *Virology* 25:193; Fields et al. (1971) *Virology* 43:569; Mayor (1965) *J. NCI* 35:919; Mbisa et al. (2000) *Virology* 272:16; Parker et al. (2002) *J. Virol.* 76:4483; Rhim et al. (1962) *Virology* 17:342; Sharpe et al. (1982) *Virology* 120:399; Silverstein et al. (1968) *J. Cell Biol.* 36:197; Silverstein et al. (1970) *Virology* 41:564; Spendlove et al. (1964) *Cancer Res.* 24:1826; Touris-Otero et al. (2004) *J. Mol. Biol.* 341:361; Touris-Otero et al. (2004) *Virology* 319:94). These inclusions are commonly called viral factories (Fields et al. supra; Parker et al. supra) or viroplasms (Touris-Otero et al. supra) and are similar to cytoplasmic inclusions formed by other viruses in the same family. In cells infected by rotaviruses or orbiviruses, for example, these structures are called viroplasms (Eichwald et al. (2004) *J. Gen. Virol.* 85:625; Silvestri et al. (2004) *J. Virol.* 78:7763) or viral inclusion bodies (Brookes (1993) *J. Gen. Virol.* 74:525; Theron et al. (1996) *Arch. Virol.* 141:1143), respectively.

Many viruses sequester their replication machinery within localized structures or surfaces in infected cells: for example, herpes simplex virus (double-stranded (ds) DNA genome, family Herpesviridae) in nuclear inclusions (reviewed in Roizman et al. (2001) Herpes simplex viruses and their replication, pp. 2231-2295. In D. M. Knipe and P. M. Howley (ed.), *Fields Virology*. Lippincott Williams & Wilkins, Philadelphia), vaccinia virus (dsDNA genome, family Poxyiridae) in cytoplasmic inclusions also called viral factories (reviewed in Moss, B. (2001) Poxyiridae: the viruses and their replication, 2637-2671. In D. M. Knipe and P. M. Howley (ed.), *Fields Virology*. Lippincott Williams & Wilkins, Philadelphia), brome mosaic virus (single-stranded (ss) RNA genome, family Bromoviridae) on the cytoplasmic face of the endoplasmic reticulum (Restrepo-Hartwig et al. (1996) *J. Virol.* 70:8908; Schwartz et al. (2002) *Mol. Cell.* 9:505), and flock house virus (ssRNA genome, family Nodaviridae) on the cytoplasmic face of mitochondria (Miller et al. (2001) *J. Virol.* 75:11664).

In early studies, reovirus factories were determined to contain fully and partially assembled viral particles, viral proteins, dsRNA, microtubules, and "kinky" filaments proposed to be intermediate filaments, but not membrane-bound structures or ribosomes (Dales (1963) *Proc. Natl. Acad. Sci. USA* 50:268; Dales et al. (1965) *Virology* 25:193; Mayor supra; Rhim et al. supra; Sharpe et al. supra; Silverstein et al. (1970) *Virology* 41:564; Spendlove et al.). The factories have a peculiarly dense consistency that distinguishes them from the adjacent cytoplasm and causes them to appear highly refractile by phase-contrast microscopy. The determinants or features of one or more viral proteins that would make them capable of forming such a matrix are not well understood.

SUMMARY OF THE INVENTION

The present invention is based in part on the discovery of particular viral polypeptide sequences that mediate the formation of inclusion bodies. The present invention describes particular polypeptides from reoviral and rotaviral proteins that modulate the formation of inclusion bodies. The present invention is directed in part to a novel method for assaying protein-protein associations, protein-nucleic acid associations, protein-membrane associations, protein-carbohydrate associations, and the like within cells. The methods described herein are broadly applicable to a variety of protein-protein interactions, protein-nucleic acid interactions, protein-membrane interactions, protein-carbohydrate interactions, and the like.

Embodiments of the present invention are directed to methods for detecting an interaction between a first polypeptide and a second polypeptide. Such methods include providing a cell expressing a first polypeptide operably linked to a viral inclusion body protein or a biologically active portion thereof, contacting the first polypeptide with the second polypeptide, allowing formation of an inclusion body, and detecting the second polypeptide in the inclusion body if the first polypeptide and the second polypeptide interact. In certain aspects, the viral inclusion body protein comprises a reoviral protein or a biologically active portion thereof from a reovirus selected from the group consisting of Orthoreovirus, Orbivirus, Rotavirus, Coltivirus, Seadornavirus, Aquareovirus, Cypovirus, Entomoreovirus, Fijivirus, Phytoreovirus and Orzavirus. In other aspects, the viral inclusion body protein is μNS or NSP5 (e.g., the entire viral inclusion body protein or a portion thereof, e.g., a carboxy-terminal one-third of the protein). In certain aspects, the second polypeptide is endogenously or exogenously expressed by the cell, such as by an expression vector.

In certain aspects, detecting the presence of the second polypeptide in an inclusion body can be performed by fluorescence microscopy. In other aspects, an automated system is used to detect the presence of the second polypeptide in an inclusion body.

Embodiments of the present invention are also directed to methods for modulating an activity of a first polypeptide. Such methods include providing a cell expressing the first polypeptide, contacting the cell with a second polypeptide operably linked to a reoviral inclusion body protein or a biologically active portion thereof, allowing formation of an inclusion body, and allowing the first polypeptide to be localized to the inclusion body such that an activity of the first polypeptide is modulated. In certain aspects, the cell expresses both the first polypeptide and the second polypeptide.

In one aspect, the first polypeptide interacts with the second polypeptide by a protein-protein interaction. In another aspect, the second polypeptide interacts with a third polypeptide by a protein-protein interaction. In certain aspects, the first polypeptide is sequestered in the cytoplasm. In other aspects, an activity of the first polypeptide is decreased or increased. In still other aspects, an activity of the first polypeptide is titrated.

Embodiments of the present invention are also directed to methods for modulating an activity of a first polypeptide. Such methods include providing a cell expressing the first polypeptide, contacting the cell with a second polypeptide operably linked to a reoviral inclusion body protein or a biologically active portion thereof, allowing formation of an inclusion body, and contacting the cell with an agent that modulates binding of the first polypeptide to the second polypeptide such that an activity of the first polypeptide is modulated. In certain aspects, the activity of the first polypeptide is decreased, increased and/or titrated.

Other embodiments of the present invention are directed to methods for identifying an agent that modulates binding of a first polypeptide to a second polypeptide. Such methods include contacting a cell expressing the first polypeptide and the second polypeptide, wherein the second polypeptide is operably linked to a reoviral inclusion body protein or a biologically active portion thereof, contacting the cell with the agent, allowing formation of an inclusion body, and detecting the presence of the first polypeptide in the inclusion body. In certain aspects, the agent is a small molecule, such as a small molecule selected from a library. In other aspects, the agent that modulates binds the first polypeptide. In other aspects, the agent increases binding of the first polypeptide to the second polypeptide or decreases binding of the first polypeptide to the second polypeptide.

Other embodiments of the present invention are directed to methods for localizing a first polypeptide to an area in a cell. Such methods include providing a cell expressing the first polypeptide, contacting the cell with a second polypeptide operably linked to a reoviral inclusion body protein or a biologically active portion thereof, allowing formation of an inclusion body, and allowing the first polypeptide to be localized to the inclusion body such that the first polypeptide is present in the localized area. In certain aspects, the localized area is in the cytoplasm. In other aspects, a function of the first polypeptide is modulated by the localization, and the function is decreased or increased.

Other embodiments of the present invention are directed to methods for detecting an interaction between two polypeptides. Such methods include providing a cell expressing library polypeptides, contacting the cell with a polypeptide operably linked to a reoviral inclusion body protein or a biologically active portion thereof, allowing formation of an inclusion body, allowing one or more library polypeptides to be localized to the inclusion body, and detecting localization of one or more library polypeptides to the inclusion body if a library polypeptide and the polypeptide operably linked to the reoviral inclusion body protein or the biologically active portion thereof interact. In certain aspects, the library polypeptides are operably linked to an epitope tag. In other aspects, the library polypeptides are operably linked to an identifiable marker.

Other embodiments of the present invention are directed to methods for identifying an agent that modulates aberrant cellular proliferation. Such methods include providing a cell expressing a polypeptide that binds to an oncoprotein or a tumor suppressor protein, wherein the polypeptide is operably linked to a viral inclusion body protein or a biologically active portion thereof, contacting the cell with the agent, allowing formation of an inclusion body, and detecting the presence of an oncoprotein or a tumor suppressor protein in the inclusion body.

In certain aspects, the oncoprotein or tumor suppressor protein is endogenously expressed, expressed by an expression vector or expressed by a virus. In other aspects, the oncoprotein is selected from the group consisting of PDGF, ERB-B, ERB-B2, K-RAS, N-RAS, C-MYC, N-MYC, L-MYC, BCL-2, BCL-1, MDM2, and a viral oncoprotein. In still other aspects, the tumor suppressor protein is selected from the group consisting of APC, DPC4, NF-1, NF-2, MTS1, RB, and p53. In certain aspects, the aberrant cellular proliferation is cancer. In other aspects, the agent decreases aberrant cellular proliferation.

Still other embodiments of the present invention are directed to compositions for detecting an agent that modulates a protein-protein interaction. Such compositions include a cell expressing an inclusion body protein or a biologically active portion thereof operably linked to a first polypeptide, and a second polypeptide that interacts with the first peptide.

Still other embodiments of the present invention are directed to kits for detecting a protein-protein interaction. Such kits include a first expression vector that expresses an inclusion body protein or a biologically active portion thereof operably linked to a cloning cassette and a second expression vector comprising a cloning cassette. In certain aspects, the kits include instructions for use.

Certain embodiments are directed to expression vectors comprising cDNA which encodes a polypeptide having at least about 85% sequence homology to SEQ ID NO:1. Other embodiments are directed to expression vectors comprising cDNA which encodes a polypeptide having an amino acid sequence of SEQ ID NO:1. In certain aspects, a host cell transfected with the expression vector is provided. In other aspects, a method of producing a polypeptide comprising culturing the host cell in an appropriate culture medium to, thereby, produce the polypeptide is provided. Embodiments of the present invention are directed to host cells expressing a fusion protein comprising a polypeptide having at least about 85% sequence homology to SEQ ID NO:1, and to host cells expressing a first polypeptide operably linked to a second polypeptide, wherein the second polypeptide comprises an amino acid sequence of SEQ ID NO:1.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

DETAILED DESCRIPTION OF THE INVENTION

Figure 1:
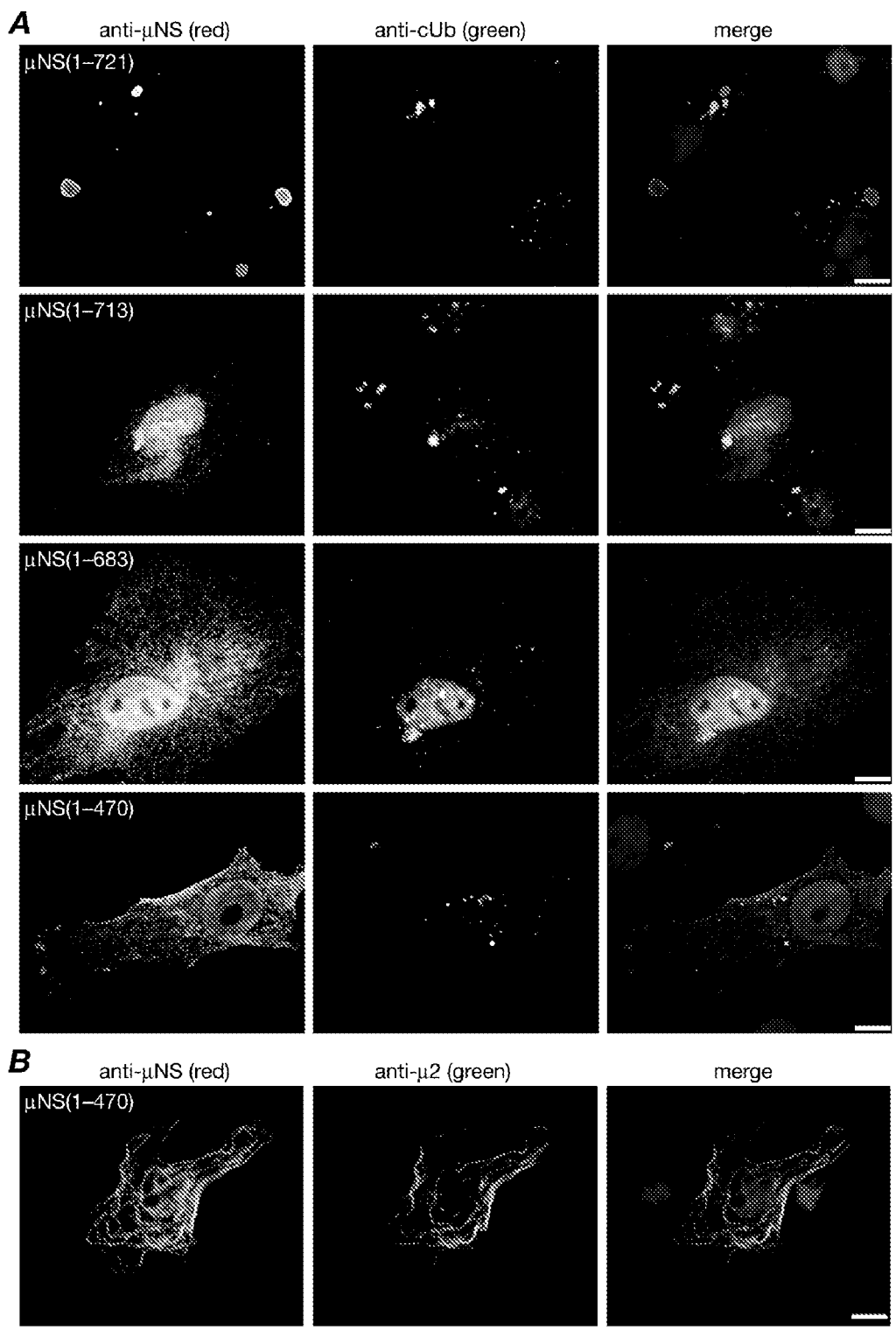
FIGS. 1A-1B depict immunofluorescence microscopy of C-terminally truncated µNS proteins. CV-1 cells were transfected with plasmids to express the indicated proteins. The cells were then fixed at 18 hours post-transfection (h.p.t.) for subsequent immunostaining. Nuclei were counterstained with 4',6-Diamidino-2-phenylindole (DAPI) (blue). Scale bars, 10 µm. (A) depicts cells immunostained with rabbit anti-µNS IgG conjugated to Texas Red (left column, red in right column) and with mouse MAb FK2 against conjugated ubiquitin (cUb) followed by goat anti-mouse IgG conjugated to Alexa 488 (center column, green in right column). (B) depicts cells immunostained with rabbit anti-µNS IgG followed by goat anti-rabbit IgG conjugated to Alexa 594 (left column, red in right column) and with rabbit anti-µ2 IgG conjugated to Alexa 488 (center column, green in right column).

The present invention provides a novel technology for identifying and characterizing protein-protein and/or protein-nucleic acid associations as they occur within cells. This approach is useful for high-throughput formats and, accordingly, can be used to screen a variety of different types of libraries to identify protein-protein and/or protein-nucleic acid associations and/or to identify molecules (e.g., large or small molecules) that modulate (e.g., increase or decrease) such associations. The present invention is particularly useful for identifying and/or modulating protein-protein and/or protein-nucleic acid associations relevant to human diseases, such as proliferative diseases and/or disorders such as cancer.

In certain embodiments of the invention, an inclusion body protein or a portion thereof is used to assay protein-protein and/or protein-nucleic acid interactions in a cell. As used herein, the term "inclusion body" refers to a macromolecular structure wherein proteins (e.g., viral inclusion body proteins) localize. Inclusion bodies may form in the cytoplasm and/or the nucleus of a cell. As used herein, the term "inclusion body protein" is intended to include, but is not limited to, a viral protein or a portion thereof that is involved in inclusion body formation. Exemplary inclusion body proteins include, but are not limited to, the orthoreovirus μNS protein, the avian reovirus μNS protein, the aquareovirus μNS protein, the rotavirus NSP5 protein, the bluetongue virus NS2 protein, and the like. As used herein, a "biologically active portion" of an inclusion body protein is intended to include an amino acid sequence sufficient for formation of and/or localization to an inclusion body.

The inclusion body proteins described herein may be derived from a variety of viruses, such as DNA or RNA viruses. As used herein, RNA viruses include, but are not limited to, virus families such as Picornaviridae (e.g., polioviruses), Reoviridae (e.g., rotaviruses), Togaviridae (e.g., encephalitis viruses, yellow fever virus, rubella virus), Orthomyxoviridae (e.g., influenza viruses), Paramyxoviridae (e.g., respiratory syncytial virus, measles virus, mumps virus, parainfluenza virus), Rhabdoviridae (e.g., rabies virus), Coronaviridae, Bunyaviridae, Flaviviridae, Filoviridae, Arenaviridae, Bunyaviridae, and Retroviridae (e.g., human T-cell lymphotropic viruses (HTLV), human immunodeficiency viruses (HIV)). As used herein, DNA viruses include, but are not limited to, virus families such as Papovaviridae (e.g., papilloma viruses), Adenoviridae (e.g., adenovirus), Herpesviridae (e.g., herpes simplex viruses), and Poxyiridae (e.g., variola viruses).

Exemplary viruses include, without limitation, viruses from the Reoviridae family, including, but not limited to, the genera *Orthoreovirus, Orbivirus, Rotavirus, Coltivirus, Seadornavirus, Aquareovirus, Cypovirus, Entomoreovirus, Fijivirus, Phytoreovirus* and *Orzavirus*.

Orthoreoviruses include, but are not limited to, mammalian orthoreoviruses (strain Lang, strain D5/Jones, Dearing and the like), avian orthoreoviruses (strain S1133, strain 176, strain SK138a and the like), Nelson Bay orthoreoviruses, baboon orthoreoviruses, rattlesnake orthoreoviruses, Ndelle virus, duck reovirus and the like.

Orbiviruses include, but are not limited to, bluetongue virus (BTV 1-24 and the like), African horse sickness virus (AHSV 1-9 and the like), changuinola virus (Almeirim virus, Altamira virus, Caninde virus, Changuinola virus, Gurupi virus, Irituia virus, Jamanxi virus, Jari virus, Monte Dourado virus, Ourem virus, Purus virus, Saraca virus and the like), Chenuda virus (Baku virus, Chenuda virus, Essaouira virus, Huacho virus, Kala Iris virus, Mono Lake virus, Sixgun City virus and the like), Chobar Gorge virus (Chobar Gorge virus, Fomede virus and the like), Corriparta virus (Acado virus, Corriparta virus CS109, Corriparta virus V654, Corriparta Virus V370, Jacareacanga virus and the like), epizootic hemorrhagic disease virus (epizootic hemorrhagic disease viruses 1-8, Ibaraki virus, isolate 318 and the like), equine encephalosis virus (EEV 1-7 and the like), Eubenangee virus (Eubenangee virus, Ngoupe virus, Pata virus, Tilligerry virus and the like), Teri virus (Teri virus, Gomoka virus, Arkonam virus and the like), Great Island virus (Above Maiden virus, Arbroath virus, Bauline virus, Broadhaven viruses (BRDV L2, M5, S7 and S10 and the like), Cape Wrath Virus, Colony virus, Colony B North virus, Ellidaey virus, Foula virus, Great Island virus, Great Saltee Island virus, Grimsey virus, Inner Farne virus, Kemerovo virus, Kenai virus, Kharagysh virus, Lundy virus, Maiden virus, Mill Door virus, Mykines virus, North Clett virus, North End virus, Nugget virus, Okhotskiy virus, Poovoot virus, Post Islands virus, St. Abb's Head virus, Shiant Islands virus, Thormodseyjarklettur virus, Tillamook virus, Tindholmur virus, Tribec virus, Vearoy virus, Wexford virus, Yaquina Head virus and the like), Lebombo virus (LEBV-1 and the like), Orungo virus (ORUV 1-4 and the like), Palyam virus (Abadina virus, Bunyip Creek virus, CSIRO village virus, D-Aguilar virus, Kasba virus, Chuzan virus, Kindia virus, Marrakai virus, Nyabira virus, Palyam virus, Petevo virus, Vellore virus and the like), Umatilla virus (Llano Seco virus, Minnal virus, Netivot virus, Umatilla virus and the like) Wad Medani virus (Seletar virus, Wad Medani virus and the like), Wallal virus (Mudjinbarry virus, Wallal virus, Wallal K virus and the like), Warrego virus (Mitchell River virus, Warrego virus, Warrego K virus and the like), and Wongorr virus (Paroo River virus, Picola virus, Wongorr virus (WGRV MRM1343, CS131, V195, V199, V595 and V1447)).

Rotaviruses include, but are not limited to, rotavirus A (simian rotavirus A/SA11 and the like), rotavirus B (RV strains IDIR, ADRV and the like), rotavirus C (porcine rotavirus C/Cowden and the like), rotavirus D (chicken rotavirus D/132 and the like), rotavirus E (porcine rotavirus E/DC-9 and the like), rotavirus F (chicken rotavirus F/A4 and the like), and rotavirus G (chicken rotavirus G/555 and the like).

Coltiviruses include, but are not limited to, Colorado tick fever virus (Colorado tick fever virus, California hare Coltivirus, CTFV S6-14-03 and the like), and Eyach virus (EYAV Germany, France-577, France-578 and the like).

Seadornaviruses include, but are not limited to Banna virus (BAV China, BAV China-HN59, BAV China-HN131, BAV China-HN191, BAV China-HN295, Indonesia-6423, Indonesia-6324, Indonesia-6969, Indonesia-7043 and the like), and Kadipiro virus (KDV Java-7075 and the like).

Aquareoviruses include, but are not limited to, Aquareovirus A (American oyster reovirus 13p2V, Angel fish reovirus, Atlantic salmon reovirus HBR, Atlantic salmon reovirus ASV, Atlantic salmon reovirus TSV, Chinook salmon reovirus DRC, Chum salmon reovirus CSV, Masou salmon reovirus MS, smelt reovirus, striped bass reovirus and the like), Aquareovirus B (Chinook salmon reovirus B, Chinook salmon reovirus LBS, Chinook salmon reovirus YRC, Chinook salmon reovirus ICR, Coho salmon reovirus CSR, Coho salmon reovirus ELC, Coho salmon reovirus SCS and the like), Aquareovirus C (golden shiner reovirus and the like), Aquareovirus D (channel catfish reovirus and the like), Aquareovirus E (turbot reovirus and the like), Aquareovirus F (Chum salmon reovirus PSR, Coho salmon reovirus SSR and the like), Chub reovirus Germany, Grass carp reovirus, hard clam reovirus, landlocked salmon reovirus, and tench reovirus.

Cypoviruses include, but are not limited to, Cypovirus 1 (*Bombyx mori* cypovirus 1, *Dendrolimus spectabilis* cypovirus 1, *Lymantria dispar* cypovirus 1 and the like), Cypovirus 2 (*Aglais urticae* cypovirus 2, *Agraulis vanillae* cypovirus 2, *Arctia caja* cypovirus 2, *Arctia villica* cypovirus 2, *Boloria dia* cypovirus 2, *Dasychira pudibunda* cypovirus 2, *Eriogaster lanestris* cypovirus 2, *Hyloicus pinastri* cypovirus 2, *Inachis io* cypovirus 2, *Lacanobia oleracea* cypovirus 2, *Malacosoma brassicae* cypovirus 2, *Mamestra brassicae* cypovirus 2, *Operophtera brumata* cypovirus 2, *Papilio machaon* cypovirus 2, *Phalera bucephala* cypovirus 2, *Pieris rapae* cypovirus 2 and the like), Cypovirus 3 (*Anaitis plagiata* cypovirus 3, *Arctia caja* cypovirus 3, *Danaus plexippus* cypovirus 3, *Gonometa rufibrunnea* cypovirus 3, *Malacosoma neustria* cypovirus 3, *Operophtera brumata* cypovirus 3, *Phlogophera meticulosa* cypovirus 3, *Pieris rapae* cypovirus 3, *Spodoptera exempta* cypovirus 3 and the like), Cypovirus 4 (*Actias selene* cypovirus 4, *Antheraea mylitta* cypovirus 4, *Antheraea pemyi* cypovirus 4 and the like), Cypovirus 5 (*Euxoa scandens* cypovirus 5, *Heliothis armigera* cypovirus 5, *Orgyia pseudosugata* cypovirus 5, *Spodoptera exempta* cypovirus 5, *Trichoplusia ni* cypovirus 5 and the like), Cypovirus 6 (*Aglais urticae* cypovirus 6, *Agrochola helvolva* cypovirus 6, *Agrochola lychnidis* cypovirus 6, *Anaitis plagiata* cypovirus 6, *Anti xanthomista* cypovirus 6, *Biston betularia* cypovirus 6, *Eriogaster lanestris* cypovirus 6, *Lasiocampa quercus* cypovirus 6 and the like), Cypovirus 7 (*Mamestra brassicae* cypovirus 7, *Noctua pronuba* cypovirus 7 and the like), Cypovirus 8 (*Abraxas grossulariata* cypovirus 8, *Heliothis armigera* cypovirus 8, *Malacosoma disstria* cypovirus 8, *Nudaurelias cytherea* cypovirus 8, *Phlogophora meticulosa* cypovirus 8, *Spodoptera exempta* cypovirus 8 and the like), Cypovirus 9 (*Agrotis segetum* cypovirus 9 and the like), Cypovirus 10 (*Aporophyla lutulenta* cypovirus 10 and the like), Cypovirus 11 (*Heliothis armigera* cypovirus 11, *Heliothis zea* cypovirus 11, *Lymantria dispar* cypovirus 11, *Mamestra brassicae* cypovirus 11, *Pectinophora gossypiella* cypovirus 11, *Pseudaletia unipuncta* cypovirus 11, *Spodoptera exempta* cypovirus 11, *Spodoptera exigua* cypovirus 11 and the like), Cypovirus 12 (*Autographa gamma* cypovirus 12, *Mamestra brassicae* cypovirus 12, *Pieris rapae* cypovirus 12, *Spodoptera exempta* cypovirus 12 and the like), Cypovirus 13 (*Polistes hebraeus* cypovirus 13 and the like), and Cypovirus 14 (*Heliothis armiogera* cypovirus 14 'A' strain, *Heliothis armiogera* cypovirus 14 'B' strain, *Choristoneura fumiferana* cypovirus and the like).

Entomoreoviruses include, but are not limited to, *Dacus oleae* reovirus, *Drosophila* F virus, *Drosophila* S virus, *Ceratitis* I virus, *Hyposoter exiguae* reovirus, *Musca domestica* reovirus, and *Diadromus pulchellus* reovirus.

Fijiviruses include, but are not limited to, Fijivirus group 1 (Fiji disease virus and the like), Fijivirus group 2 (rice black streaked dwarf virus, maize rough dwarf virus, mal del rio cuarto virus, pangola stunt virus and the like) Fijivirus group 3 (oat sterile dwarf virus and the like), Fijivirus group 4 (garlic dwarf virus and the like), and Fijivirus group 5 (*Nilaparvata lugens* reovirus).

Phytoreoviruses include, but are not limited to, rice dwarf virus (isolates A, B, S, H and China), rice gall dwarf virus, wound tumor virus, and tobacco leaf enation phytoreovirus.

Oryzaviruses include, but are not limited to, rice ragged stunt virus (strains That, Philippine and Indian) and *echinochloa* ragged stunt virus.

Unassigned species in the family include, but are not limited to, *Cimex lactularis* reovirus, *Macropipus depurator* P reovirus, *Carcinus mediterraneus* W2 virus, *Porcelio dilatatus* reovirus, and *Buthyus occitanus* reovirus. Rotaviruses are discussed further in *Fields Virology* (Estes, M. (2001) "Rotaviruses and their Replication," pages 2637-2671, D. M. Knipe and P. M. Howley (ed.), Lippincott Williams & Wilkins, Philadelphia), incorporated herein by reference in its entirety for all purposes.

As used herein, the term "protein-protein interaction" is intended to include, but is not limited to, interactions between two or more proteins, protein fragments, polypeptides, or combinations thereof, including protein complexes. The terms protein, protein fragment and polypeptide are used interchangeably herein.

Embodiments of the present invention are also directed to detecting interactions between a protein (e.g., a protein, protein fragment, polypeptide or the like) and a nucleic acid sequence (e.g., a polynucleotide, an oligonucleotide or the like), e.g., a "protein-nucleic acid interaction." Nucleic acid sequences include, but are not limited to, DNA and RNA.

As used herein, the terms "bind," "binding," "interact" and "interacting" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions are much weaker than covalent interactions, but play a major role in determining the three-dimensional structure of macromolecular structures. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994, chapter 3, pages 88-91, incorporated herein by reference in its entirety for all purposes.

In certain aspects of the invention, an activity of a polypeptide is modulated when the polypeptide is recruited to an inclusion body. Recruitment may occur via a protein-protein interaction between two or more polypeptides. Recruitment of a polypeptide to an inclusion body can be used to titrate one or more activities of a polypeptide. Recruitment may be affected (e.g., increased or decreased) by an agent that modulates a protein-protein interaction, which is discussed further below. As used herein, the terms "modulate an activity of a polypeptide" and "modulating an activity of a polypeptide" refer to an increase or a decrease of a polypeptide activity (e.g., an increase or decrease of a biological activity of the protein). For example, a polypeptide activity may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more. A polypeptide activity may be increased by 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 550%, 600%, 650%, 700%, 750%, 800%, 850%, 900%, 950%, 1000% or more.

As used herein, the term "polypeptide activity" refers to a variety of cellular activities including, but not limited to, binding activities, such as the ability to interact with one or more of the following: polypeptides, polypeptide complexes, nucleic acid sequences, carbohydrates, bacteria, viruses and the like; and/or mediating one or more cellular activities such as cell signaling (intracellular and extracellular), cell cycle, cell division, cell differentiation, cell proliferation, transcription, translation, membrane fusion, cell transport (intracellular and extracellular), endocytosis, exocytosis, protein folding, protein processing, nucleic acid processing, nucleic acid repair, polypeptide degradation and the like.

In certain aspects of the invention, proteins may be associated (e.g., operably linked, covalently attached or non-covalently attached) with one or more identifiable markers. Identifiable markers include, without limitation, visually detectable markers that may be selected for and/or screened for using technologies such as fluorescence activated cell sorting (FACS) or microfluidics. Examples of detectable markers include various enzymes, prosthetic groups, fluorescent markers, luminescent markers, bioluminescent markers, and the like.

Examples of suitable fluorescent proteins include, but are not limited to, yellow fluorescent protein (YFP), green fluorescence protein (GFP), enhanced green fluorescent protein (EGFP), cyan fluorescence protein (CFP), cyanine (e.g., Cy3, Cy5, Cy3.5 and the like), umbelliferone, coumarin, pyrene, fluorescein, fluorescein isothiocyanate, carboxyfluorescein (FAM), hexachlorofluorescein (HEX), tetrachlorofluorescein (TET), dichlorotriazinylamine fluorescein, carboxynapthofluorescein, rhodamine (green or blue), carboxyrhodamine, carboxyeosin, erythrosine, dansyl chloride, phycoerythrin, Alexa Fluor (e.g., Alexa Fluor 350, −405, −430, −488, −532, −546, −555, −568, −594, −633, −647, −660, −680, −700, −750 and the like), Oyster (e.g., Oyster 556, −645, −656 and the like) Oregon Green, Texas Red, Marina Blue, Pacific Blue, Cascade, Blue, Cascade Yellow, Lucifer Yellow, ROX (carboxy-X-rhodamine), TAMRA (carboxytetramethylrhodamine), BODIPY, JOE, MAX, EDANS, PyMPO, NBD-X and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. Identifiable markers also include radioactive compounds such as $^{125}$I, $^{35}$S, $^{14}$C, or $^{3}$H. Identifiable markers are commercially available from a variety of sources.

Detection of identifiable markers may be performed by direct or indirect (e.g., using a microscope, camera or other device) visual inspection or using a detection means such as a fluorescence-detecting device or scanner, photometric device (e.g., a spectrophotometer), mass spectrometer, signal-activated cell sorting device (e.g., a fluorescence-activated cell sorter, or FACS) or other fluidics device. Methods of screening identifiable markers are known in the art, and kits and equipment for screening identifiable markers are commercially available.

In certain aspects of the invention, an identifiable marker, an epitope tag and/or a reoviral inclusion body protein or a biologically active portion thereof is operatively linked to a polypeptide sequence. The term "operably linked" is intended to mean that the nucleic acid sequence encoding the identifiable marker, epitope tag and/or reoviral inclusion body protein or a biologically active portion thereof is linked to a nucleic acid sequence encoding the polypeptide sequence in a manner which allows for expression of the identifiable marker, epitope tag and/or reoviral inclusion body protein or a biologically active portion thereof and the polypeptide sequence. An identifiable marker, epitope tag and/or reoviral inclusion body protein or a biologically active portion thereof operably linked to a polypeptide may be present on a nucleic acid molecule, including without limitation a nucleic acid vector, which molecule is introduced into a host cell by transfection, transformation or other means known in the art.

As used herein, the term "epitope tag" refers to a portion of a molecule to which an antibody binds. An epitope can be composed of sugars, lipids, amino acids and the like. In certain aspects, an epitope is an amino acid sequence operably linked to a polypeptide sequence. Epitope tags include, but are not limited to, c-myc (EQKLISEEDL) (SEQ ID NO:2), HA (YPYDVPDYA) (SEQ ID NO:3), His$_6$ (HHHHHH) (SEQ ID NO:4), FLAG (DYKDDDDKC) (SEQ ID NO:5), T7 (MASMTGGQQMG) (SEQ ID NO:6), V5 (GKPIPNPLLGLDST) (SEQ ID NO:7), VSV-G (YTDIEMNRLGK) (SEQ ID NO:8), ECS (DDDDK) (SEQ ID NO: 9), DYKDDDDK (SEQ ID NO:10), AU1 (DTYRYI) (SEQ ID NO:11), AU5 (TDFYLK) (SEQ ID NO:12), E-Tag (GAPVPYPDPLEPR) (SEQ ID NO:13), S-Tag (KETAAAKFERQHMDS) (SEQ ID NO:14), Glu-Glu (EYMPME) (SEQ ID NO:15), HSV (SQPELAPEDPED) (SEQ ID NO:16), KT3 (KPPTPPPEPET) (SEQ ID NO:17), DIG (digoxigenin), Glutathione-S-transferase (GST), biotin, β-galactosidase, chloramphenicol-acetyl transferase (CAT) and the like, as well as any of the identifiable markers discussed further herein.

In certain aspects, an agent for detecting a polypeptide present in an inclusion body is an antibody capable of binding to the polypeptide, such as an antibody with a detectable label. Antibodies can be polyclonal or monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. An example of indirect labeling is the detection of a primary antibody using a fluorescently labeled secondary antibody. Antibodies of the invention can bind to a variety of amino acid sequences such as, for example, to the polypeptide sequence, to an identifiable marker operably linked to the polypeptide sequence, or to an epitope tag operably linked to the polypeptide sequence.

Antibodies can be generated by standard techniques. For example, polyclonal antibodies can be prepared by immunizing a suitable subject with an immunogen, such as a polypeptide sequence of interest, an identifiable marker, an epitope tag and the like. The anti-immunogen antibody titer in the immunized subject can be monitored over time by standard techniques, such as with an enzyme linked immunosorbent assay (ELISA) using immobilized immunogen. If desired, the antibody molecules directed against the immunogen can be isolated from the subject (e.g., from the blood) and further purified by well known techniques, such as protein A chromatography to obtain the IgG fraction. At an appropriate time after immunization, e.g., when the anti-immunogen antibody titers are highest, antibody-producing cells can be obtained from the subject and used to prepare monoclonal antibodies by standard techniques, such as the hybridoma technique originally described by Kohler and Milstein ((1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) *J. Biol. Med.,* 54:387-402; M. L. Gefter et al. (1977) *Somatic Cell Genet.* 3:231-36. Each reference is incorporated herein in its entirety for all purposes). Antibodies are also commercially available from companies such as Bethyl Laboratories, Inc (Montgomery, Tex.), Abcam Inc. (Cambridge, Mass.), Rockland Immunochemicals, Inc. (Gilbertsville, Pa.), QED Bioscience Inc. (San Diego, Calif.) and Covance Research Products, Inc. (Berkeley, Calif.).

Certain aspects of the invention pertain to vectors, such as expression vectors, containing a nucleic acid encoding an inclusion body protein (or a biologically active portion thereof) operably linked to a nucleic acid encoding a first polypeptide (e.g., a bait polypeptide or a binding partner); and/or containing a nucleic acid encoding a second polypeptide (e.g., a prey polypeptide or a binding partner). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

As used herein, a "cloning cassette" refers to a nucleic acid construct capable of directing the expression of a gene/coding sequence of interest. Such cassettes can be constructed into a "vector," "vector construct," "donor vector," "expression vector" or "gene transfer vector" in order to transfer the expression cassette into target cells. Thus, the term includes, in non-limiting fashion, cloning and expression vehicles, as well as viral vectors.

Embodiments of the invention are directed to a first nucleic acid or polypeptide sequence having a certain sequence identity or percent homology to a second nucleic acid or polypeptide sequence, respectively. Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.). One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization*, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., at 60° C. or 65° C.

A first polynucleotide is "derived from" a second polynucleotide if it has the same or substantially the same base-pair sequence as a region of the second polynucleotide, its cDNA, complements thereof, or if it displays sequence identity as described above. A first polypeptide is derived from a second polypeptide if it is (i) encoded by a first polynucleotide derived from a second polynucleotide, or (ii) displays sequence identity to the second polypeptides as described above. In the present invention, when a recombinase is "derived from a phage" the recombinase need not be explicitly produced by the phage itself, the phage is simply considered to be the original source of the recombinase and/or nucleic acid sequences that encode it. Recombinases can, for example, be produced recombinantly or synthetically, by methods known in the art, or alternatively, recombinases may be purified from phage infected bacterial cultures.

As used herein, the term "substantially purified" is intended to include, but is not limited to, isolation of a substance (e.g., compound, polynucleotide, protein, polypeptide, polypeptide composition and the like) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well known in the art and include, but are not limited to, ion-exchange chromatography, affinity chromatography, sedimentation according to density and the like.

In certain embodiments, nucleic acid sequences encoding on or more of the polypeptides described herein may be introduced into an expression vector and transfected into a host cell. The host cell may be any prokaryotic or eukaryotic cell. For example, a polypeptide of the invention may be expressed in bacterial cells, such as *E. coli*, insect cells (baculovirus), yeast, plant, or mammalian cells. The host cell may be supplemented with tRNA molecules not typically found in the host so as to optimize expression of the polypeptide. Ligating the polynucleotide construct into an expression vector, and transforming or transfecting into hosts, either eukaryotic (yeast, avian, insect or mammalian) or prokaryotic (bacterial cells), are standard procedures. Examples of expression vectors suitable for expression in prokaryotic cells such as *E. coli* include, for example, plasmids of the types: pBR322-derived plasmids, pEMBL-derived plasmids, pEX-derived plasmids, pBTac-derived plasmids and pUC-derived plasmids; expression vectors suitable for expression in yeast include, for example, YEP24, YIP5, YEP51, YEP52, pYES2, and YRP17; and expression vectors suitable for expression in mammalian cells include, for example, pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors.

Vectors can be targeted for delivery to host cells via conventional transformation or transfection techniques. In certain aspects, the introduced vector and the target cells together are capable of targeted recombination. As used herein, the terms "transformation" and "transfection" are intended to refer to a variety of art-recognized techniques for introducing an exogenous nucleic acid sequence (e.g., DNA) into a host cell, including calcium phosphate or calcium chloride co-precipitation, DEAE-dextran-mediated transfection, lipofection, electroporation, optoporation, injection and the like. Suitable methods for transforming or transfecting cells can be found in Sambrook et al., *Current Protocols in Molecular Biology*. John Wiley & Sons, Inc., 1998; *Methods in Enzymol.* (Vols. 68, 100, 101, 118, and 152-155) (1979, 1983, 1986 and 1987); and *DNA Cloning*, D. M. Clover, Ed., IRL Press, Oxford (1985); incorporated herein by reference in their entirety for all purposes), and other laboratory manuals.

A host cell can be any prokaryotic or eukaryotic cell. For example, host cells can be cells such as yeast, insect cells, plant cells, reptilian cells, fish cells, amphibian cells (such as *Xenopus* cells), or mammalian cells (such as Chinese hamster ovary cells (CHO), mouse cells, African green monkey kidney cells (CV-1, COS), fetal human cells (293T) or other human cells). Other suitable target cells are known to those skilled in the art. Both cultured and explanted cells may be used according to the invention. The present invention is also adaptable for in vivo use using viral vectors including, but not limited to, replication defective retroviruses, adenoviruses, adeno-associated viruses and the like. For in vivo use, marker selection can be applied to the entire organism such as, for example, by using an automated worm sorter (Union Biometrica, Zurich Switzerland).

Target cells useful in the present invention include human cells including, but not limited to, embryonic cells, fetal cells, and adult stem cells. Human stem cells may be obtained, for example, from a variety of sources including embryos obtained through in vitro fertilization, from umbilical cord blood, from bone marrow and the like. In one aspect of the invention, target human cells are useful as donor-compatible cells for transplantation, e.g., via alteration of surface antigens of non-compatible third-party donor cells, or through the correction of genetic defect in cells obtained from the intended recipient patient. In another aspect of the invention, target cells, including without limitation human cells, are useful for the production of therapeutic proteins, peptides, antibodies and the like.

The host cells of the invention can also be used to produce nonhuman transgenic, knockout or other genetically-modified animals. Such animals include those in which a gene or nucleic acid is altered in part, e.g., by small or large deletions and/or insertions of exogenous nucleic acid sequences. For example, in one embodiment, a host cell of the invention is a fertilized oocyte or an embryonic stem cell into which the addition or deletion of one or more nucleic acids has been performed. Such host cells can then be used to create nonhuman transgenic animals in which exogenous detectable translation product sequences have been introduced into their genome. As used herein, a "transgenic animal" is a non-human animal, such as a mammal, e.g., a rodent such as a guinea pig, rat, mouse or the like, in which one or more of the cells of the animal includes one or more exogenous genes. Other examples of transgenic animals include non-human primates, cows, goats, sheep, pigs, rabbits, ferrets, dogs, cats, chickens, amphibians, and the like. An exogenous gene is exogenous DNA that is integrated into the genome of a cell from which a transgenic animal develops and which remains in the genome of the mature animal. A knockout is the removal of endogenous DNA from a cell from which a knockout animal develops, which remains deleted from the genome of the mature animal. Methods for generating transgenic and knockout animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al., and in Hogan, B., *Manipulating the Mouse Embryo*, (Cold Spring Harbor Laboratory Press, Cold Spring Harbor, N.Y., 1986), incorporated herein by reference in their entirety for all purposes.

In certain embodiments, the present invention is directed to methods of screening modulators of protein-protein and/or protein-nucleic acid interactions. In one embodiment, a cell expressing an inclusion body protein (or a biologically active portion thereof) operably linked to a bait polypeptide can be used to screen for compounds that modulate the ability of the bait polypeptide to interact with one or more polypeptides (i.e., binding partners). Binding partners may be endogenously expressed by the cell, and/or exogenously expressed, e.g., by an expression vector. The ability of the modulator to increase or decrease a protein-protein and/or protein-nucleic acid interaction can be determined by observing an increased presence or a decreased presence, respectively, of the binding partner in an inclusion body using the assays described herein.

In certain embodiments, an assay is a cell-based assay comprising contacting a cell expressing an inclusion body protein (or a biologically active portion thereof) operably linked to a first polypeptide and determining the ability of a test compound to modulate (e.g. inhibit or promote) the ability of the first polypeptide to bind a second polypeptide (i.e., binding partner), i.e., the ability of the compound to modulate one or more protein-protein and/or protein-nucleic acid interactions. Determining the ability of the test compound to modulate protein-protein and/or protein-nucleic acid interactions can be accomplished, for example, by determining the ability of a compound to modulate recruitment of the second polypeptide to an inclusion body.

In yet another embodiment, an assay of the present invention is a cell-free assay in which an inclusion body protein, or a biologically active portion thereof, operably linked to a first polypeptide is contacted with a test compound and the ability of the first polypeptide to bind to a second polypeptide (e.g., a binding partner) is determined as described above.

In one aspect, modulators of protein-protein and/or protein-nucleic acid interactions can be identified using peptide or compound libraries by methods known to those of skill in the art. Test compounds (e.g., peptides) can be isolated from cells or tissue sources using standard protein purification techniques, be produced by recombinant DNA techniques or synthesized chemically by standard methods. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection (Lam, K. S. (1997) *Anticancer Drug Dis.* 12:145, incorporated herein by reference in its entirety for all purposes).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233 (incorporated herein by reference in their entirety for all purposes).

Libraries of compounds may be presented in solution (e.g., Houghten (1992) *Biotechniques* 13:412), or on beads (Lam (1991) *Nature* 354:82), chips (Fodor (1993) *Nature* 364:555), bacteria (Ladner, U.S. Pat. No. 5,223,409), spores (Ladner, U.S. Pat. No. 5,223,409), plasmids (Cull et al (1992) *Proc. Natl. Acad. Sci. USA* 89:1865) or on phage (Scott and Smith (1990) *Science* 249:386; Devlin (1990) *Science* 249:404; Cwirla et al. (1990) *Proc. Natl. Acad. Sci. USA* 87:6378;

Felici (1991) *J. Mol Biol.* 222:301; and Ladner, supra) (incorporated herein by reference in their entirety for all purposes).

In one embodiment, the present invention is directed to identifying an agent that modulates aberrant cellular proliferation, such as cancer. Aberrant cellular proliferation is intended to include, but is not limited to, inhibition of proliferation including rapid proliferation. As used herein, the term "disorder associated with aberrant cellular proliferation" includes, but is not limited to, disorders characterized by undesirable or inappropriate proliferation of one or more subset(s) of cells in a multicellular organism. The term "cancer" refers to various types of malignant neoplasms, most of which can invade surrounding tissues, and may metastasize to different sites (*PDR Medical Dictionary* 1st edition (1995)). The terms "neoplasm" and "tumor" refer to an abnormal tissue that grows by cellular proliferation more rapidly than normal and continues to grow after the stimuli that initiated proliferation is removed (*PDR Medical Dictionary* 1st edition (1995)). Such abnormal tissue shows partial or complete lack of structural organization and functional coordination with the normal tissue which may be either benign (i.e., benign tumor) or malignant (i.e., malignant tumor).

Certain embodiments of the present invention are directed to the modulation of oncoproteins and/or tumor suppressor proteins. Oncoproteins are intended, without limitation, to refer to proteins and/or peptides that are capable of inducing cell transformation. Oncoproteins include, but are not limited to, cellular proteins such as PDGF, ERB-B, ERB-B2, K-RAS, N-RAS, C-MYC, N-MYC, L-MYC, BCL-2, BCL-1, MDM2 and the like. Oncoproteins also include, but are not limited to, viral proteins from RNA and/or DNA tumor viruses such as hepatitis B viruses, SV40 viruses, polyomaviruses, adenoviruses, herpes viruses, retroviruses and the like. Tumor suppressor proteins are intended, without limitation, to refer to proteins or polypeptides that can suppress or block aberrant cellular proliferation. Tumor suppressor proteins include, but are not limited to, cellular proteins such as APC, DPC4, NF-1, NF-2, MTS1, RB, p53 and the like.

This invention is further illustrated by the following examples, which should not be construed as limiting. The contents of all references, patents and published patent applications cited throughout this application are hereby incorporated by reference in their entirety for all purposes.

EXAMPLE I

P53-SV40 T-Antigen Protein-Protein Association

A novel technology is presented herein to model protein-protein interactions in vivo. The association between cellular p53 and viral (SV40) T antigen (T-Ag) is used as a model of protein-protein associations with relevance to cancer. In one aspect of the invention, this system will be used with a high-throughput format in order to screen small-molecule libraries for agents that block the p53/T-Ag association within cells. In another aspect of the invention, this technology will be used to screen modulators of protein-protein interactions using, for example, a variety of different proteins that have a known association with cancer.

Figure 9:
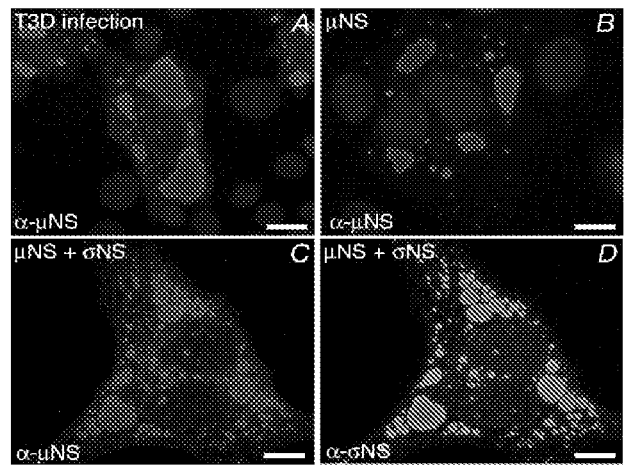
FIG. 9 depicts cells analyzed for GFP fluorescence or immunostained for antigen. Upper panels depict reovirus-infected (A) or plasmid-transfected (B-D) CV-1 cells that were immunostained for the reovirus protein µNS (α-µNS) or σNS (α-σNS). The transfected cells received plasmid to express either µNS alone (B) or both µNS and σNS (C, D). Lower panels depict plasmid-transfected CV-1 cells that were analyzed for inherent fluorescence of green fluorescent protein (GFP) or immunostained for reovirus protein σNS (α-σNS). The transfected cells received plasmid to express both σNS and either GFP/µNS(471-721) (A, B) or µNS(1-41)/GFP/µNS(471-721) (C, D). Bar, 10 µm.
Figure 9:
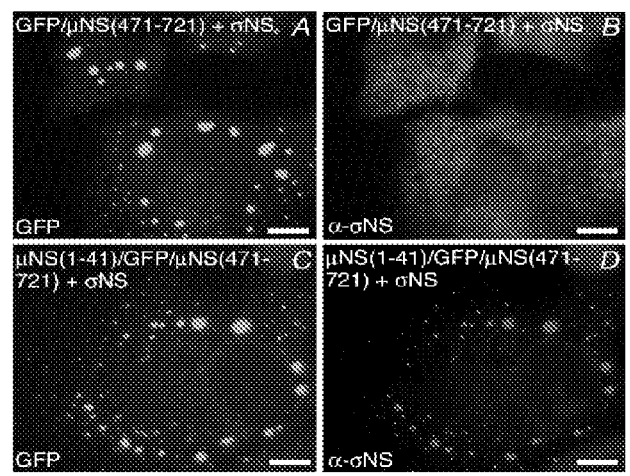
Figure 10:
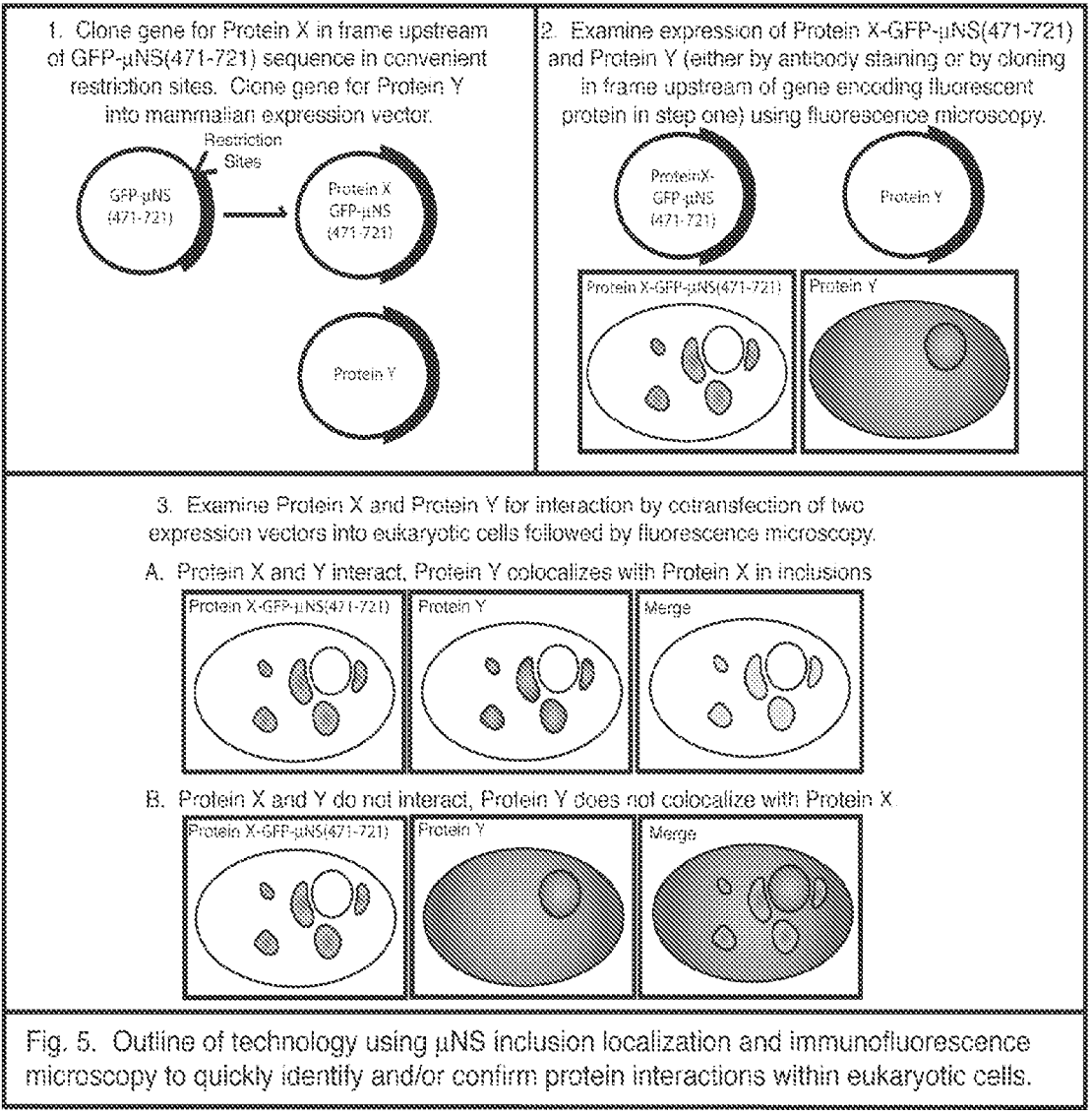
FIG. 10 depicts a schematic outlining the use of µNS inclusion localization. Immunofluorescence can be used to quickly identify and/or confirm protein-protein interactions within eukaryotic cells. In step 1, the gene for Protein X is cloned in frame upstream of GFP-µNS(471-721) sequence using restriction sites. The gene for Protein Y is cloned into a mammalian expression vector. In step 2, expression of Protein X-GFP-µNS(471-721) and Protein Y is examined by antibody staining or by detecting GFP using fluorescence microscopy. In step 3, protein-protein interactions between Protein X and Protein Y are detected after co-transfecting the two expression vectors into eukaryotic cells followed by fluorescence microscopy. (A) shows Protein Y co-localizing with Protein X in inclusion bodies, indicative of a protein-protein interaction between Protein Y and Protein X. (B) shows the absence of Protein Y and Protein X co-localization, indicating that Protein Y and Protein X do not interact with one another.

Within infected cells, reoviruses induce the formation of distinctively large cytoplasmic structures, commonly called "viral factories," to which most of the viral proteins are recruited and in which the assembly of new viral particles occurs (FIG. 9A, upper). The reovirus non-structural protein μNS, when expressed in the absence of any other reovirus protein, is uniquely capable of forming cytoplasmic structures that appear very similar to the factories (FIG. 9B, upper). In addition, when co-expressed with certain other of the reovirus proteins, the μNS protein recruits these other viral proteins into the factory-like structures in the absence of infection (FIGS. 9C, 9D, upper).

A region encompassing the C-terminal 251 amino acid residues of the 721-residue μNS protein was determined to be necessary and sufficient for forming the factory-like structures (FIG. 9A, lower), but not for mediating associations with the other reovirus proteins (FIG. 9B, lower). This 251-residue region, μNS(471-721), retained its capacity to form factory-like structures when fused to an amino- or carboxyl-terminal tag, such as green fluorescent protein (GFP) (FIG. 9A, lower). In addition, GFP/μNS(471-721) served as an effective platform for presenting more amino-terminal regions of μNS for their functions in binding to other viral proteins and recruiting these other proteins into the factory-like structures. For example, μNS residues 1 to 40 are necessary for μNS association with reovirus proteins μ2 and σNS. μNS(1-41)/GFP/μNS(471-721) includes a sufficiently large portion of μNS for recruiting both μ2 and σNS into the factory-like structures (FIGS. 9C, 9D, lower).

Figure 8:
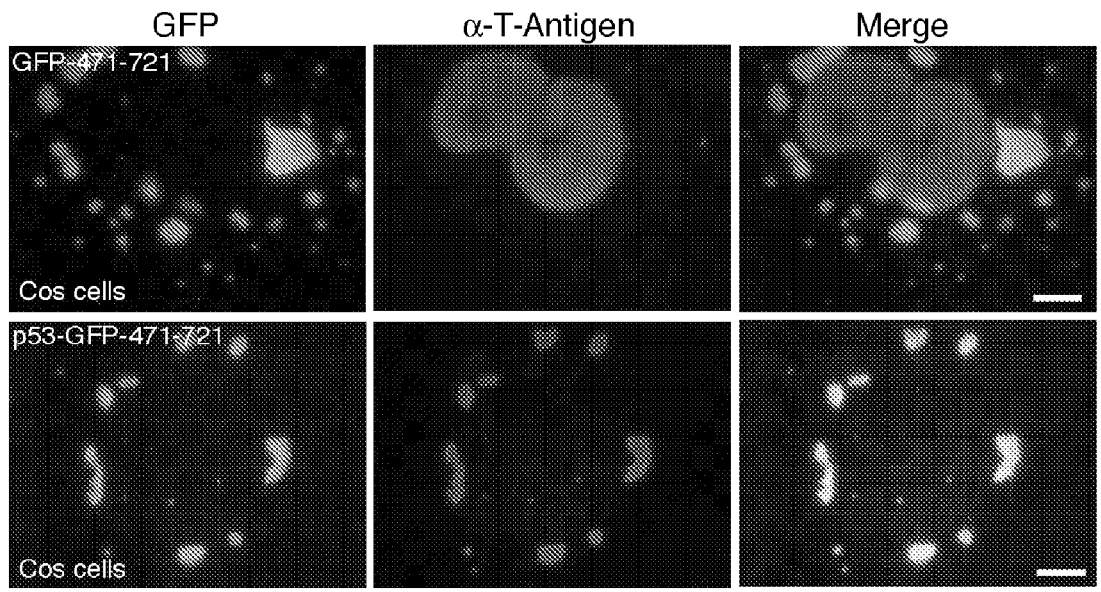
FIG. 8 depicts specific recruitment of the SV40 T Antigen to inclusion structures in the presence but not the absence of a p53-GFP-471-721 fusion protein. The top panel depicts COS cells expressing endogenous T antigen in the presence of GFP-471-721 fusion protein (upper) or p53-GFP-471-721 fusion protein (lower). The bottom panel depicts COS cells expressing a T Antigen-HA fusion protein in the presence of GFP-471-721 fusion protein (upper) or p53-GFP-471-721 fusion protein (lower). Green, GFP; Red, anti-T-Antigen; Yellow, merge of GFP and T-antigen images.
Figure 8:
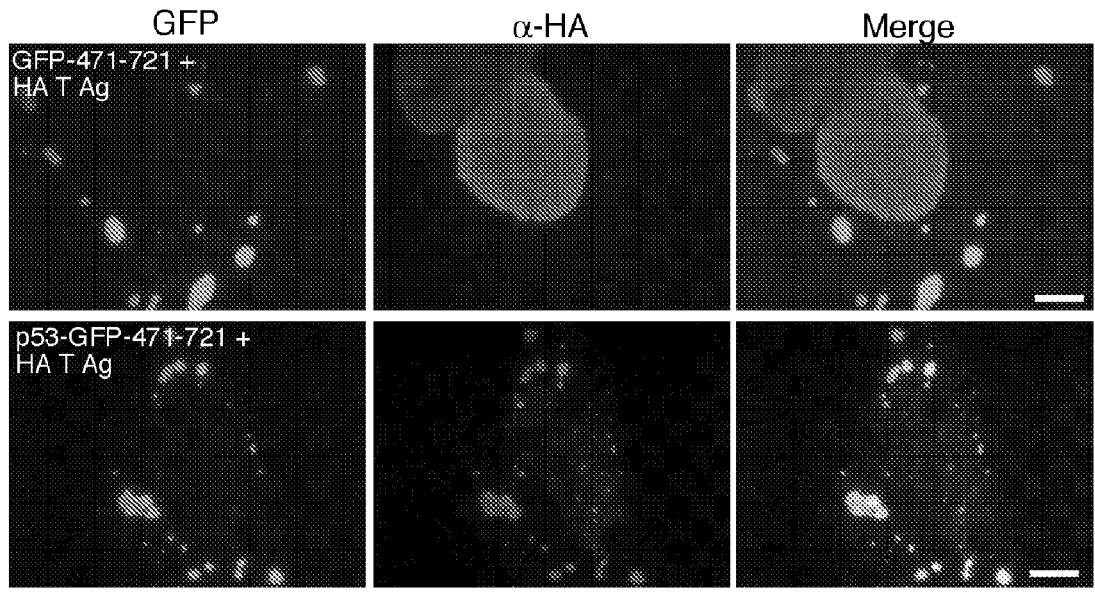

Whether a foreign protein, when expressed as a fusion to this platform, might be sufficiently well presented to allow one or more of its protein-interaction partners to be recruited to the factory-like structures was tested. Cellular p53 was expressed as part of the fusion protein (p53/GFP/μNS(471-721)) to examine the capacity of this fusion to recruit SV40 T-Ag, a known interaction partner of p53 (reviewed in Ali et al. and Pipas et al.), into the factory-like structures. Whereas the control protein GFP/μNS(471-721) failed to recruit T-Ag into the factory-like structures (FIG. 8), p53/GFP/μNS(471-721) showed strong recruitment activity in the majority of cells (FIG. 8) and clearly demonstrated recruitment activity in essentially all cells in which the fusion protein and T-Ag were expressed. Specific recruitment of SV40 T-Ag in the presence of p53 was also observed (FIGS. 8A-8B). These results indicate that this technology is broadly applicable to studies of protein-protein associations in general including, but not limited to, the following protocols.

The present invention is useful as a facile means for demonstrating known or suspected protein-protein associations in cells. The methods and compositions described herein are useful for mapping the protein region(s) involved in a given association to be placed on relatively small peptides on one or both sides of the association. In one aspect, protein or polypeptide interactors can be identified for a given "bait" protein or polypeptide that is expressed as a fusion with μNS(471-721). For example, a cDNA expression library of potential interactors, constructed to express cellular (or viral, bacterial, etc.) proteins with an easily identifiable and distinguishable tag, such as red fluorescent protein (RFP), can be screened.

This technology can also be used to identify inhibitors of a particular, targeted protein-protein association. For example, libraries of small molecules can be screened to identify compounds that block the association of two or more proteins within the factory-like structures, without affecting the formation of the factory-like structures themselves by the GFP/μNS(471-721) fusion protein. This technology can be used with a variety of protein-protein associations relevant to human cancers in order to screen modulators of the protein-protein associations.

Access to libraries of small-molecule inhibitors will be obtained through the Harvard Institute of Chemistry and Cell Biology available at iccb.med.harvard.edu/) and other laboratories that specialize in work at the chemistry-biology interface. Adaptation to high-throughput format can be done in stages, serially addressing different challenges to improve the overall approach. One modification to the basic protocol is to have the p53/μNS(471-721) and T-antigen proteins both tagged with a fluorescent protein, eliminating the need for any immunostaining in the setting of the screen. To that end GFP- and RFP-tagged versions of T antigen and RFP-tagged p53/μNS(471-721) will be generated for use in the appropriate combinations to allow the p53/T-Ag association to be visualized within the factory-like structures in living CV-1 or other cells. Another modification will be to express two associating proteins from a viral vector in order to eliminate the need for plasmid co-transfections in the setting of the screen and also to increase the fraction of cells expressing both proteins. A non-replicating retrovirus/lentivirus vector is useful in this regard. Alterations of the delivery method will be performed without reducing, or only minimally reducing, the capacity of the tagged p53/μNS(471-721) and T-antigen proteins to strongly colocalize in most or all cells.

Screening can be done in a 384-well microplate format. Results of the screen can be acquired on a fluorescence microscope with appropriate optics for distinguishing the different tags. The results can be acquired manually, by a human operator, or can be acquired in an automated manner, in digital format, for high throughput analysis. Sample compounds that block the p53/T-antigen association (e.g., RFP- and GFP-tagged proteins that do not colocalize) can be identified by reviewing the digital images, again either manually or in an automated manner. Active compounds will be confirmed by repeat testing. Compounds that reduce expression of the proteins or formation of the factory-like structures (i.e., false positives) can be detected visually. For active compounds that pass these tests, additional experiments would be performed to ascertain whether the compound's effects are specific to the p53/T-antigen association, without affecting the normal, desired functions of p53.

The present invention is also useful for investigating other associations in addition to p53 and T-antigen. A number of other viruses with oncogenic potential in humans that encode proteins that bind to p53 (reviewed in Collot-Teixeira) will be used. For example, the E6 protein of human papillomaviruses, BZLF1 protein of Epstein-Barr virus, and HBx protein of hepatitis B virus are examples of such p53-interacting proteins that will be used with the assays described herein. Protein-specific antibodies will be obtained and used to immunostain localizations of each of these proteins expressed with p53/GFP/μNS(471-721) or p53/RFP/μNS(471-721). RFP- or GFP-tagged versions of each of the tested proteins will be constructed for respective co-expression with p53/GFP/μNS(471-721) or p53/RFP/μNS(471-721).

EXAMPLE II

C Terminus of μNS is Required for Forming Factory-Like Inclusions

To determine if the C terminus of μNS was required for sequestration in factory-like inclusions, M3 gene constructs were engineered to express a series of truncated μNS proteins that lacked increasing numbers of residues from the C terminus (see Table 1). Each of these plasmids was transfected into CV-1 cells, and the cell lysates were subjected to SDS-PAGE followed by immunoblotting with polyclonal anti-μNS serum (Broering et al. (2000) *J. Virol.* 74:5516). The results verified expression of an appropriately sized, μNS-derived protein from each construct. To determine the intracellular distribution of the C-terminally truncated μNS proteins, CV-1 cells were separately transfected with each of the plasmids and later fixed and immunostained with polyclonal anti-μNS antibodies (FIG. 1A, left and right columns). In addition, the cells were coimmunostained with MAb FK2, which recognizes conjugated ubiquitin (Fujimuro et al. (1994) *FEBS Letts.* 349:173), to determine if any of these proteins were substantially misfolded and targeted for degradation by the ubiquitin-proteasome system (FIG. 1A, center and right columns). Each of the C-terminally truncated proteins was diffusely distributed in the cytoplasm and nucleus, in clear contrast to full-length μNS, which collected in globular inclusions as expected (FIG. 1A). All of these truncated proteins were negative for forming factory-like inclusions (summarized in FIG. 2), accordingly, some portion of the smallest region deleted from the C terminus of μNS, residues 714 to 721, is required for inclusion formation. None of the truncated proteins appeared aggregated or strongly colocalized with conjugated ubiquitin (FIG. 1A), indicating they were not substantially misfolded. Table 1 below is a summary of construct, enzymes and expected size of the expressed μNS truncation.

TABLE 1

| Construct | Enzymes | Size (kDa) |
|---|---|---|
| pCI-M3(1-713) | XhoI, NheI | 79.3 |
| pCI-M3(1-700) | XhoI, NheI | 78.0 |
| pCI-M3(1-683) | SalI$^d$, NheI | 76.1 |
| pCI-M3(1-470) | KpnI (blunt), SalI | 52.0 |
| pCI-M3(1-362) | KpnI (blunt), SalI | 39.9 |
| pCI-M3(1-221) | KpnI (blunt), SalI | 23.9 |
| pCI-M3(1-173) | SacI (blunt), SalI | 18.7 |
| pCI-M3(173-721) | EcoRI, SalI | 61.6 |
| pCI-M3(221-721) | EcoRI, SalI | 56.4 |
| pCI-M3(363-721) | EcoRI, SalI | 40.3 |
| pCI-M3(471-721) | EcoRI, SalI | 28.2 |

Each construct was designed to express a truncated μNS protein comprising the indicated amino-acid residues. Unless otherwise noted, pGEM-4Z plasmids from Table 3 were digested with the indicated enzymes to remove the truncated M3 genes. In some cases, one of the resulting fragment termini was converted to a blunt end (blunt) with T4 DNA polymerase before ligation to pCI-neo. pCI-M3(T3D)(1-683) was subcloned from pFastBac-M3(T1L)(1-683) as described in Materials and Methods.

Figure 2:
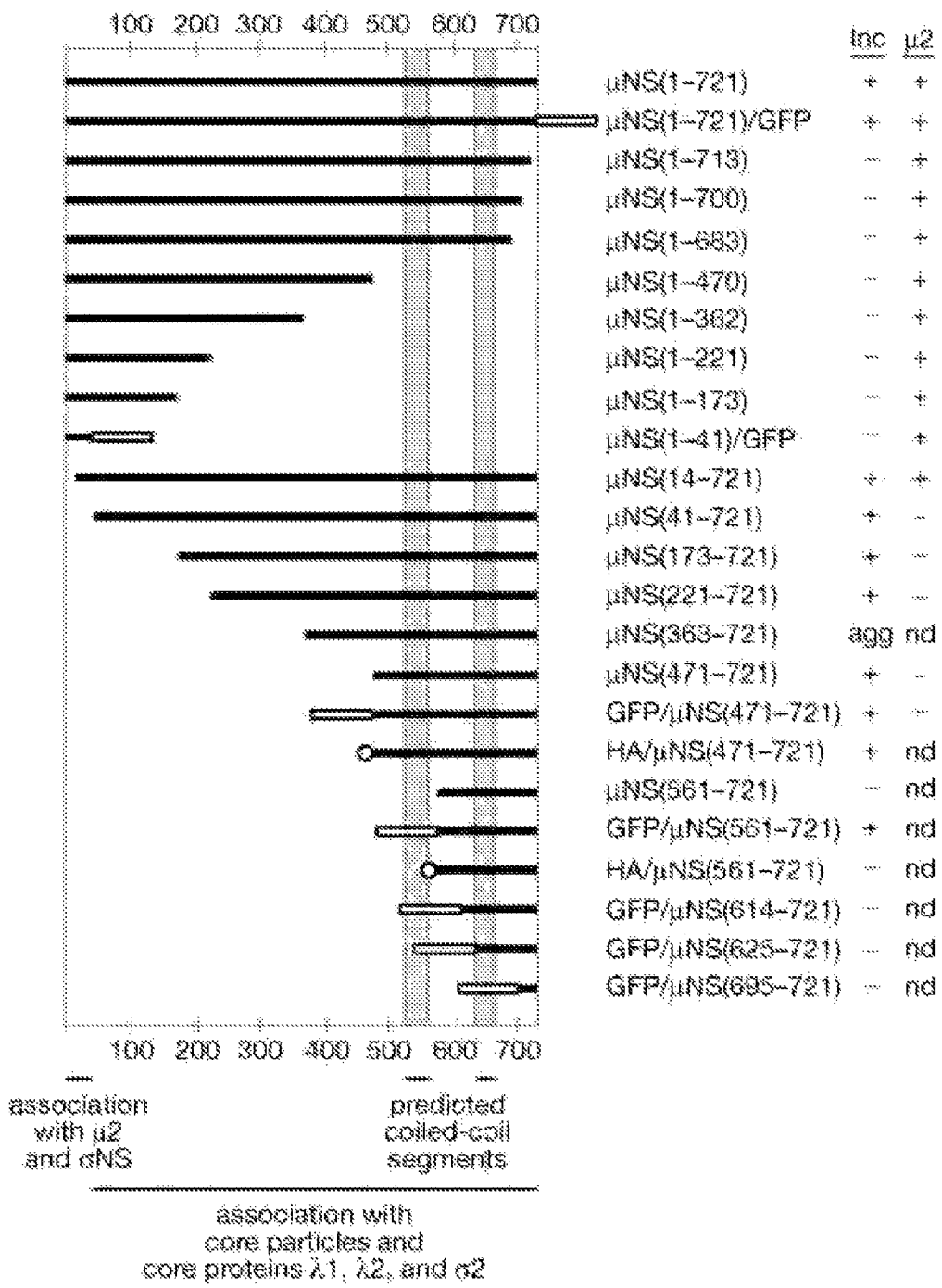
FIG. 2 depicts a schematic of µNS truncations and their activities. The full-length µNS protein is indicated by a horizontally elongated black bar spanning residues 1 to 721 (positions numbered above and below). The µNS truncation mutants are also shown as black bars spanning the approximate portion of µNS that each represents. Enhanced *A. victoria* GFP fused to the N or C terminus of µNS in some cases is represented by an open bar. An influenza HA epitope fused to the N terminus of µNS in some cases is represented by an open circle. Approximate extents of the coiled-coil segments predicted by Multicoil are indicated by vertically elongated gray bars. The capacity of each protein to form factory-like inclusions in transfected cells (Inc) and to colocalize with T1L µ2 in transfected cells (µ2) is indicated as positive (+), negative (−), or not determined (nd). Localized structures that co-stained for conjugated ubiquitin were concluded to be aggregates of misfolded protein (agg). Results for µNS(1-721), µNS(1-721)/GFP, µNS(1-41)/GFP, µNS(14-721), and µNS(41-721) have been reported previously (Broering (2002) *J. Virol.* 76:8285; Miller et al. (2003) *J. Virol.* 77:4566).

All of the C-terminally truncated μNS proteins appeared to be partially localized to the nucleus (FIG. 1A, left column), even though μNS(1-683), μNS(1-700), and μNS(1-713) were above the 60-kDa limit for passive diffusion through nuclear pores (reviewed in Quimby et al (2001) *Cell. Mol. Life Sci.* 58:1766) (Table 1). In addition, at least some of the truncated proteins appeared to be excluded from nucleoli (FIG. 1A, left column). When coexpressed with μ2 (T1L), each of the C-terminally truncated proteins strongly colocalized with μ2 on microtubules (FIG. 1B; summarized in FIG. 2). This was expected because each protein included μNS residues 1 to 41, which are known to be sufficient for association with β2 (Broering (2002) *J. Virol.* 76:8285; Miller et al. (2003) *J. Virol.* 77:4566).

EXAMPLE III

N-Terminal 470 Residues of μNS are not Required for Forming Factory-Like Inclusions, but Affect Inclusion Shape To identify the minimal region of μNS required for inclusion formation, M3 gene constructs were engineered to express a series of truncated μNS proteins that lacked increasing numbers of residues from the N terminus (Table 1). Each of these plasmids was transfected into CV-1 cells, and the cell lysates were subjected to SDS-PAGE followed by immunoblotting with the anti-μNS serum (Broering et al. (2000) *J. Virol.* 74:5516). The results verified expression of an appropriately sized, μNS-derived protein from each construct.

Figure 3:
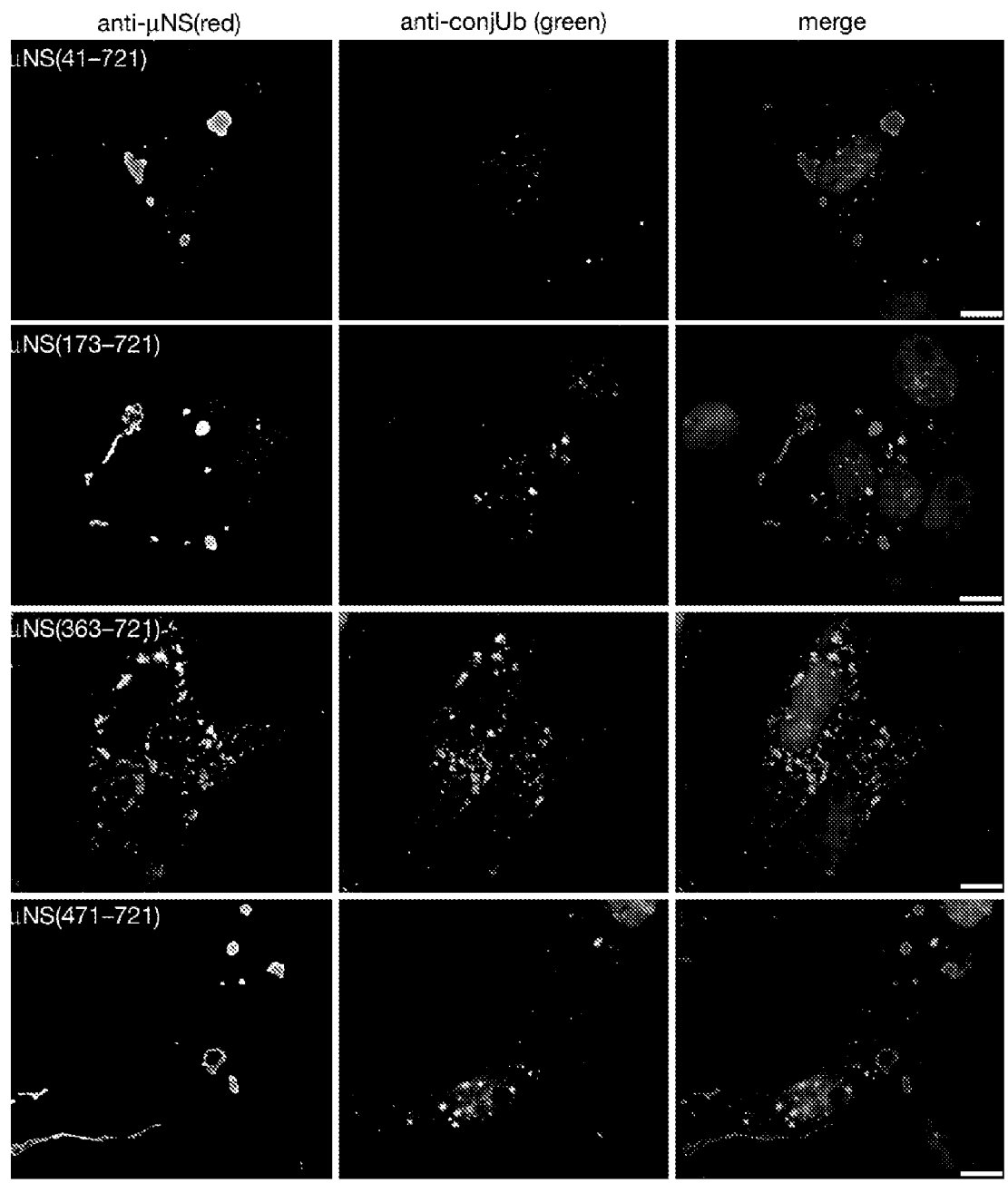
FIG. 3 depicts immunofluorescence microscopy of N-terminally truncated µNS proteins. CV-1 cells were transfected with plasmids to express the indicated proteins. The cells were then fixed and stained as described for FIG. 1A. Scale bars, 10 µm.

The intracellular distribution of each of the N-terminally truncated μNS proteins was determined as described above for the C-terminal truncations, including coimmunostaining with MAb FK2. With the exception of μNS(363-721), which showed a distinctly aggregated pattern and strongly colocalized with conjugated ubiquitin (FIG. 3), each of the N-terminally truncated proteins collected in globular inclusions (FIG. 3, left and right columns). However, the proteins missing more than the 40 N-terminal residues of μNS often formed inclusions with more elongated shapes and enclosed fenestrations than those formed by full-length μNS or μNS(41-721) (FIG. 3, left and right columns). Although these inclusions had altered morphologies, they did not colocalize with conjugated ubiquitin (FIG. 3, center and right columns), indicating that these truncated proteins were not substantially misfolded. The behavior of μNS(363-721), on the other hand, indicated that it was in fact largely misfolded. When coexpressed with μ2(T1L), none of the N-terminally truncated μNS proteins colocalized with μ2 on microtubules or in inclusions (summarized in FIG. 2). This was expected because each of these proteins lacks μNS residues 14 to 40, which are known to be required for association with μ2 (Broering (2002) *J. Virol.* 76:8285; Miller et al. (2003) *J. Virol.* 77:4566). From the results summarized in FIG. 2, it was concluded that μNS residues 471 to 721 are a sufficient part of μNS for forming factory-like inclusions. These residues encompass the two predicted coiled-coil segments of μNS, the intervening "linker" between these segment, and the C-terminal "tail" that follows the second predicted coiled-coil segments (McCutcheon et al. supra). Given the altered morphologies of the inclusions formed by μNS proteins lacking more than the 40 N-terminal residues, it was also concluded that a portion of residues 41 to 172 plays a distinguishable role in modulating inclusion morphology.

EXAMPLE IV

Residues 561 to 721 of μNS are Sufficient for Allowing a GFP-Tagged Protein, but Not an HA-Tagged or Untagged Protein, to Form Factory-Like Inclusions To determine whether a region of μNS smaller than residues 471 to 721 may be sufficient for inclusion formation, and also to allow more ready detection of these smaller proteins, constructs were generated to express GFP fused to the N terminus of selected μNS truncations (Table 2). Each of these plasmids was transfected into CV-1 cells, and the cell lysates were subjected to SDS-PAGE followed by immunoblotting with GFP-specific MAb JL-8. The results verified production of an appropriately sized, GFP- and μNS-derived fusion protein from each construct (FIG. 4A).

TABLE 2

| Construct | Forward Primer | Expressed Protein | Size (kDa) |
|---|---|---|---|
| pEGFP-C1-M3(471-721) | Not applicable | GFP/μNS(471-721) | 57.1 |

TABLE 2-continued

| Construct | Forward Primer | Expressed Protein | Size (kDa) |
|---|---|---|---|
| pEGFP-C1-M3(561-721) | CGGAATTCGTGTAG TCTGGATATGTATT TGAGACACCAC (SEQ ID NO: 18) | GFP/μNS(561-721) | 46.3 |
| pEGFP-C1-M3(614-721) | CGGAATTCGGAAGC GGCTGCCAAATGCC AAACTG (SEQ ID NO: 19) | GFP/μNS(614-721) | 40.1 |
| pEGFP-C1-M3(625-721) | CGGAATTCGATGGA CTTGACTCAGATGA ATGGAAAGC (SEQ ID NO: 20) | GFP/μNS(625-721) | 39.1 |
| pEGFP-C1-M3(695-721) | CGGAATTCGATGGC CTCCCTTCTATCAG CCACTCCT (SEQ ID NO: 21) | GFP/μNS(695-721) | 31.1 |

In Table 2 above, each construct was designed to express a GFP fusion including the indicated amino-acid residues of μNS. Forward primers are written 5' to 3'. In an EcoRI site added near the 5' end of each is underlined. In each of these proteins, GFP was fused to the N terminus of the μNS region. The data underneath the size heading is the expected size of the expressed fusion protein.

To determine the intracellular distribution of each fusion protein, CV-1 cells were transfected and later immunostained with the GFP-specific MAb. Non-fused GFP was diffusely distributed in the cytoplasm and nucleus, and GFP fused to the C terminus of full-length μNS (μNS/GFP) collected in globular inclusions as previously shown (Broering (2002) *J. Virol.* 76:8285) (also see FIG. 4B). GFP fused to the N terminus of μNS(471-721) (GFP/μNS (471-721)) also collected in inclusions (FIG. 4B), which appeared similar to those formed by μNS(471-721) (FIG. 3) or μNS/GFP (FIG. 4B). GFP fused to the N terminus of μNS(561-721) collected in inclusions as well, although a small fraction of the transfected cells (~13%) displayed a diffuse distribution of this protein (FIG. 4B and data not shown). In contrast, GFP fused to the N terminus of μNS(614-721), μNS(625-721), or μNS(695-721) was diffusely distributed in the cytoplasm and nucleus of most or all cells expressing them (FIG. 4B and data not shown). From these results, we conclude that residues 561 to 721 are a sufficient part of μNS in GFP fusions for forming factory-like inclusions (summarized in FIG. 2), albeit at a lower efficiency than full-length μNS or μNS(471-721). The first predicted coiled-coil segment (McCutcheon et al. supra) is thus dispensable for inclusion formation by a μNS-GFP fusion. On the other hand, some portion of residues 561 to 613, in the linker between the two predicted coiled-coil segments, is required.

Figure 5:
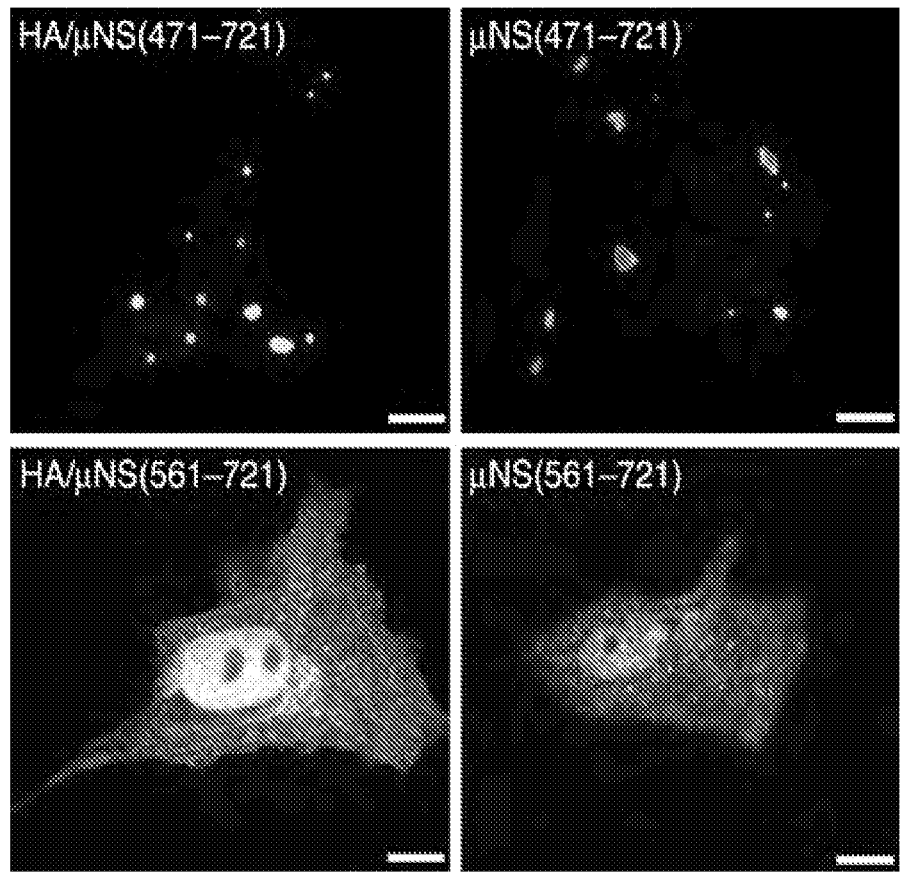
FIG. 5 depicts immunofluorescence microscopy of hemagglutinin (HA)-tagged or untagged versions of µNS(561-721) and µNS(471-721). CV-1 cells were transfected with plasmids to express the proteins as indicated. The cells were then fixed at 18 h.p.t. and immunostained either with mouse MAb HA.11 for the influenza HA epitope followed by goat anti-mouse IgG conjugated to Alexa 488 (left panels) or with rabbit anti-µNS IgG followed by goat anti-rabbit IgG conjugated to Alexa 594 (right panels). Scale bars, 10 µm.

Given that *A. victoria* GFP is known to weakly dimerize (Campbell (2002) *Proc. Natl. Acad. Sci. USA* 99:7877), and also that GFP/μNS (561-721) was less efficient at forming factory-like inclusions than was GFP/μNS(471-721), it was hypothesized that the GFP tag may partially complement an otherwise-required contribution of the first predicted coiled-coil segment of μNS for forming inclusions. Therefore, another version of μNS(561-721), this one fused to an epitope of influenza virus HA (Wilson et al. (1984) *Cell* 37:767) at its N terminus (HA/μNS(561-721)), was tested. Following expression in transfected CV-1 cells and immunostaining with tag-specific MAb HA.11, HA/μNS(561-721) was diffusely distributed in the cytoplasm and nucleus and thus not concentrated in inclusions (FIG. 5). Fusion of the HA tag to the N terminus of μNS(471-721) (HA/μNS(471-721)), in contrast, caused little or no reduction in its capacity to form factory-like inclusions (FIG. 5). A third version of μNS(561-721), this one lacking any tag, was also generated and tested. Following expression in transfected CV-1 cells and immunostaining with anti-μNS antibodies, untagged μNS(561-721) was diffusely distributed in the cytoplasm and nucleus and thus not concentrated in inclusions (FIG. 5). Untagged μNS (471-721) tested in parallel formed factory-like inclusions (FIG. 5) as seen in preceding experiments (see FIG. 3). Based on these results, it was concluded that the more N-terminal predicted coiled-coil segment of μNS was required for inclusion formation in the absence of a fusion tag such as GFP that can independently self-associate.

EXAMPLE V

Figure 4:
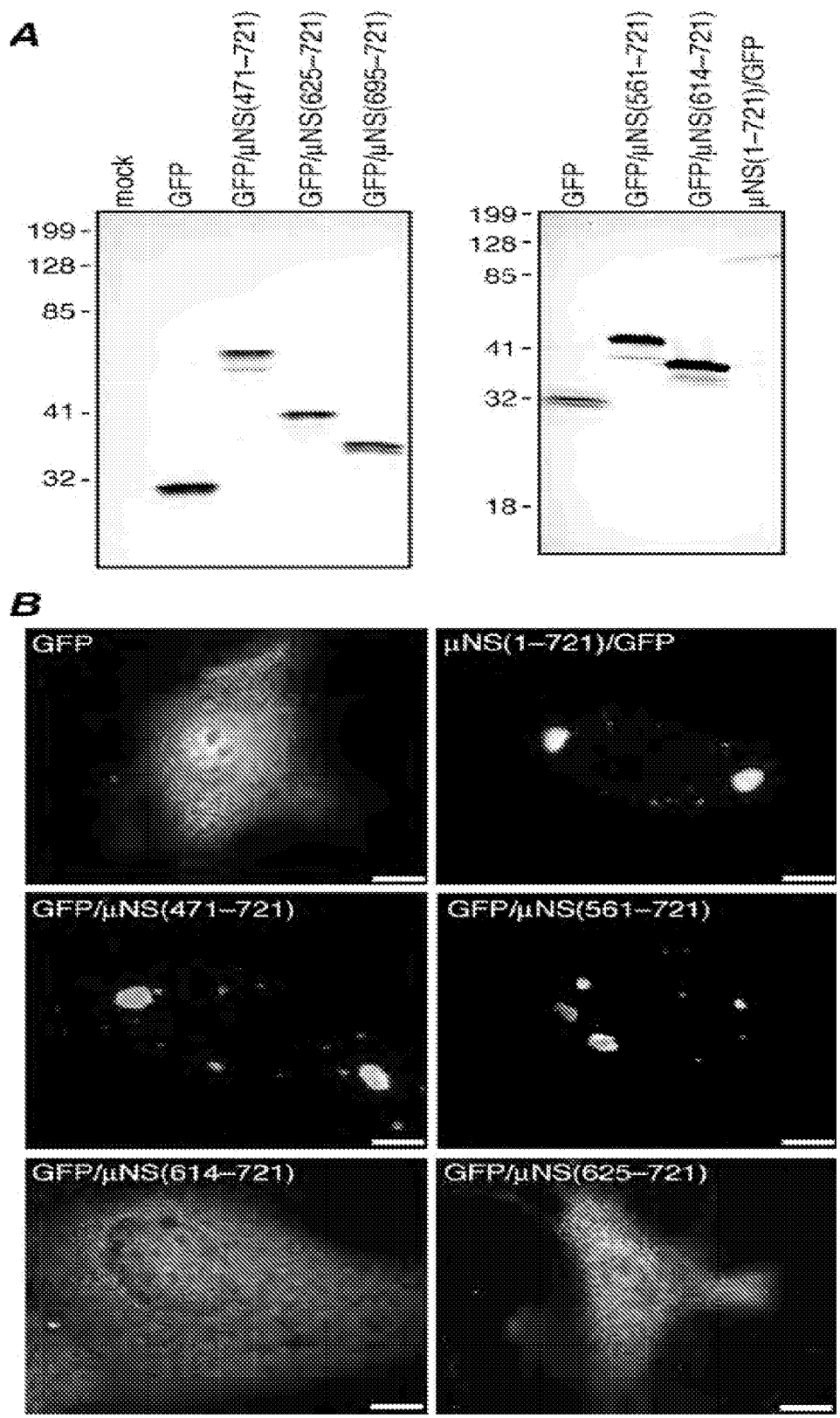
FIGS. 4A-4B depict immunoblotting and immunofluorescence microscopy of green fluorescent protein (GFP)-tagged derivatives of µNS. CV-1 cells were transfected with plasmids to express GFP or µNS-GFP fusions as indicated and then analyzed at 18 h.p.t. by immunoblotting (A) or immunofluorescence microscopy (B). Scale bars, 10 µm. (A) depicts whole cell lysates were separated by SDS-PAGE, transferred to nitrocellulose, and immunoblotted with mouse MAb JL8 for GFP followed by goat anti-mouse IgG conjugated to alkaline phosphatase. Positions of molecular weight markers are indicated (in kDa) to the left of each panel. (B) depicts cells immunostained after fixation with mouse MAb JL8 for GFP followed by goat anti-mouse IgG conjugated to Alexa 488.
Figure 6:
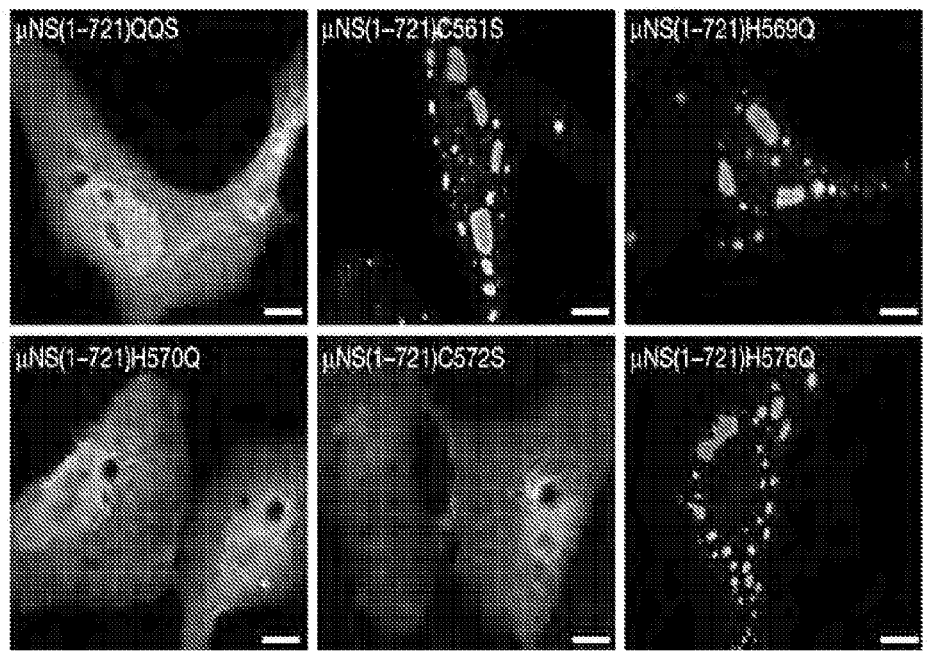
FIGS. 6A-6B depict sequence conservation in the "linker" region of µNS homologs and immunofluorescence microscopy of µNS proteins with mutations at His and/or Cys residues in the consensus motif. (A) depicts sequence conservation. Sequences are shown in single-letter code, with position numbers indicated at left and right. The consensus motif was defined by comparing the illustrated region from the µNS homologs of three mammalian orthoreoviruses (mORV), twelve avian orthoreoviruses (aORV) (all identical in this region), and two aquareoviruses (AqRV) (both identical in this region). Conserved positions are highlighted by being boxed. Asterisks indicate conserved positions corresponding to His570 and Cys572 in mammalian orthoreovirus µNS. These and other His and Cys residues in or near the consensus motif are highlighted by being circled. (B) depicts immunofluorescence microscopy. CV-1 cells were transfected with plasmids to express the indicated proteins. The cells were then fixed at 18 h.p.t. and immunostained both with rabbit anti-µNS IgG conjugated to Oregon Green and with mouse MAb FK2 for conjugated ubiquitin followed by goat anti-mouse IgG conjugated to Alexa 594. Nuclei were counterstained with DAPI. Only the anti-µNS staining is shown since no co-localization with FK2 staining was apparent. Scale bars, 10 µm. CONSENSUS is set forth as SEQ ID NO:22; mORV T1L is set forth as SEQ ID NO:23; mORV T2J is set forth as SEQ ID NO:24; mORV T3D is set forth as SEQ ID NO:25; aORV isolates (12) is set forth as SEQ ID NO:26; AqRV isolates (2) is set forth as SEQ ID NO:27.

Putative Metal-Chelating Residues His570 and Cys572 are Required for Factory-Like Inclusion Formation In an effort to identify specific residues in μNS that may be required for inclusion formation, the deduced protein sequences of μNS homologs from mammalian and avian orthoreoviruses as well as from aquareoviruses were compared. (Attoui et al. (2002) *J. Gen. Virol.* 83:1941; McCutcheon et al. supra; Touris-Otero et al. (2004) *Virology* 319:94). In total, the μNS homologs derived from seventeen isolates in the three groups: three mammalian isolates from the *Orthoreovirus* genus, twelve avian isolates from the *Orthoreovirus* genus, and two piscine isolates from the *Aquareovirus* genus. The overall identity scores for any two μNS homologs from separate groups were small, below 30% in each case (Attoui et al. supra; Touris-Otero et al. (2004) *Virology* 319:94). Despite this degree of divergence, the C-terminal one-third of each of these μNS homologs contains two predicted coiled-coil segments, of similar lengths and spacing, separated by a linker and followed by a C-terminal tail, as previously described for the mammalian and avian isolates (McCutcheon et al. supra; Touris-Otero et al. (2004) *Virology* 319:94). Interestingly, in the linker between the predicted coiled-coil segments, a small consensus motif common to all of the examined μNS homologs was identified (FIG. 6A). This sequence, Ile/Leu-x-x-Tyr-Leu-x-x-His-Thr/Val-Cys-Ile/Val-Asn (SEQ ID NO:22) (where x represents non-conserved positions), includes two residues (underlined) with strong potential to chelate transition-metal ions such as $Zn^{2+}$. The two residues correspond to His570 and Cys572 in the mammalian orthoreovirus μNS proteins. Each of the μNS homologs contains other His and/or Cys residues flanking the consensus motif, but the position and spacing of these residues is not conserved among the examined sequences (FIG. 6A). In mammalian orthoreovirus μNS, the other conserved His and Cys residues in this region are Cys561, His569, and His576. The consensus motif spans residues 563 to 574 in the mammalian orthoreovirus μNS proteins and is thus near the beginning of the minimal C-terminal region of μNS that was shown above to be sufficient for inclusion formation in GFP fusions (FIG. 4).

To determine if the conserved residues with metal-chelating potential in the consensus motif are important for inclusion formation, constructs encoding Gln (Q) substitutions for both His570 and the adjacent residue, His569, as well as a Ser (S) substitution for Cys572 were generated (FIG. 6A). The constructs were generated with all three of these mutations in the setting of either full-length μNS or μNS(471-721). CV-1 cells were transfected with these mutant plasmids and co-stained the cells with anti-μNS antibodies and MAb FK2 for conjugated ubiquitin. Both proteins, designated μNS(1-721) QQS and μNS(471-721)QQS, were diffusely distributed in the cytoplasm and nucleus (FIG. 6B and data not shown), and neither strongly colocalized with conjugated ubiquitin (data not shown). This distribution was in sharp contrast to the inclusions in which both full-length μNS and μNS(471-721) concentrated (see previous figures), demonstrating that one or more of residues His569, His570, and Cys572 is important for inclusion formation.

Next, constructs encoding single mutations at residues Cys561 (to Ser), His569 (to Gln), His 570 (to Gln), Cys572 (to Ser), or His576 (to Gln) were generated within full-length μNS. The mutant plasmids were transfected into CV-1 cells, and the cells were co-stained with anti-μNS antibodies and MAb FK2 for conjugated ubiquitin. Both μNS(1-721)H570Q and μNS(1-721)C572S were diffusely distributed in the cytoplasm and nucleus (FIG. 6B). In contrast, μNS(1-721)C561S, μNS(1-721)H569Q, and μNS(1-721)H576Q all collected in globular inclusions indistinguishable from those formed by wild-type μNS (FIG. 6B). None of the mutant proteins strongly colocalized with conjugated ubiquitin. From these findings, it was determined that His570 and Cys572 are specifically required for μNS to form factory-like inclusions in transfected cells.

EXAMPLE VI

σNS Recruitment to Factory-Like Inclusions Containing μNS Residues 1 to 12 Connected by GFP to μNS Residues 471 to 721

Figure 7:
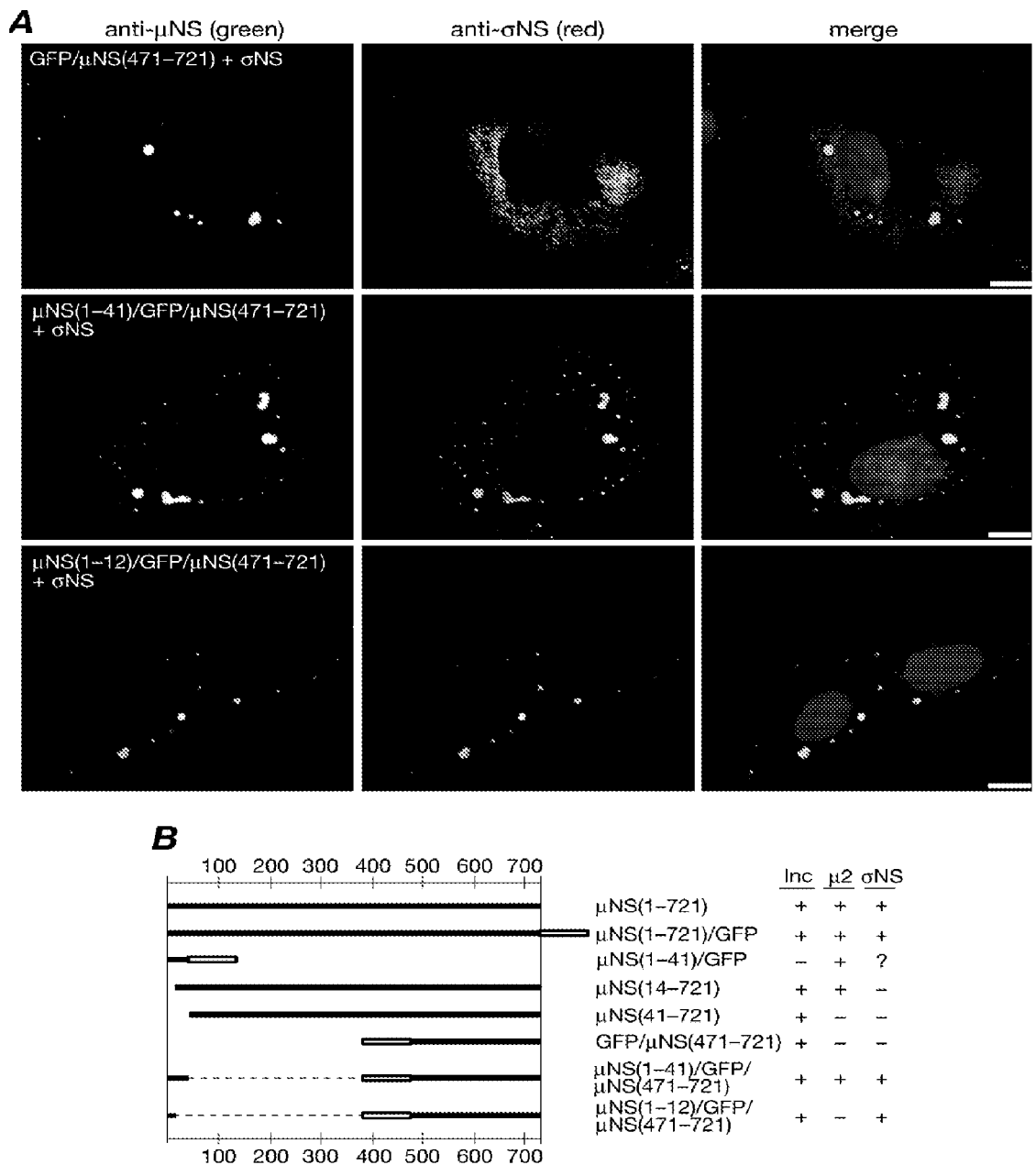
FIGS. 7A-7B depict immunofluorescence microscopy of σNS coexpressed with µNS-GFP fusions. (A) depicts CV-1 cells transfected with plasmids to express the proteins indicated. The cells were then fixed at 18 h.p.t. and immunostained with σNS-specific mouse MAb 3E10 followed by goat anti-mouse IgG conjugated to Alexa 594 (center column, red in right column). GFP-containing fusions were visualized directly (left column, green in right column). Nuclei were counterstained with DAPI (blue). Scale bars, 10 µm. (B) depicts a summary of the fusions and their activities. See FIG. 2 legend for explanations of most details. Dashed lines indicate internally deleted regions of µNS. The capacity of each protein to colocalize with T1L σNS in transfected cells (σNS) is indicated as positive (+), negative (−), or unknown (?).

Upon determining that GFP/μNS (471-721) collected in factory-like inclusions in transfected cells (FIG. 4B), it was recognized that this protein provided a new platform on which to assay protein-protein associations through redistribution to its distinctive inclusions. When GFP/μNS(471-721) was coexpressed with σNS, σNS remained diffusely distributed in the cytoplasm and nucleus and did not colocalize with the GFP/μNS (471-721) inclusions (FIG. 7A). This was expected, because some portion of μNS residues 1 to 13 is required for recruiting σNS to μNS inclusions (Miller et al. supra).

To determine if μNS residues 1 to 41 can direct recruitment of σNS to the inclusions of GFP/μNS(471-721), a plasmid was constructed to express these residues fused to the N terminus of GFP/μNS(471-721). When expressed in transfected CV-1 cells, this protein (μNS(1-41)/GFP/μNS 13(471-721)) collected in inclusions similar to those formed by μNS (471-721) or GFP/μNS(471-721) (data not shown). When σNS was coexpressed with μNS(1-41)/GFP/μNS(471-721) and coimmunostained with anti-σNS MAb 3E10 (Becker et al. (2001) *J. Virol.* 75:1459) and the anti-μNS serum, σNS strongly colocalized with the μNS(1-41)/GFP/μNS(471-721) inclusions (FIG. 7A). This was in stark contrast to the diffuse distribution of σNS expressed alone (Miller et al. (2001) *J. Virol.* 75:11664) or coexpressed with GFP/μNS(471-721) (FIG. 7A). When coexpressed with μ2, μNS(1-41)/GFP/μNS (471-721) was redistributed to filamentous inclusions (data not shown), as expected because of the presence of μNS residues 14 to 40 (also see FIGS. 2 and 6B). Id. These results demonstrate that μNS residues 41 to 470 are dispensable for recruiting σNS (summarized in FIG. 7B).

A plasmid was also constructed to express μNS residues 1 to 12 fused to the N terminus of GFP/μNS(471-721). When expressed in transfected CV-1 cells, this protein, μNS (1-12)/

GFP/μNS(471-721), collected in factory-like inclusions (data not shown). Moreover, when coexpressed, σNS was strongly recruited to the μNS(1-12)/GFP/μNS(471-721) inclusions (FIG. 7A). When coexpressed with μ2, μNS(1-12)/GFP/μNS (471-721) was not redistributed to filamentous inclusions (data not shown), as expected because of the absence of μNS residues 13 to 41. Id. These results demonstrate that μNS residues 13 to 470 are dispensable for recruiting σNS (summarized in FIG. 7B) and indicate that μNS residues 1 to 12 can be sufficient for this association.

EXAMPLE VII

Discussion

Current Summary of μNS Functional Regions

Truncation/deletion analyses have been a fruitful approach for identifying discrete regions of μNS involved in its different activities. The results presented herein demonstrate that the C-terminal one-third of μNS (residues 471 to 721) is a sufficient part of this protein for forming factory-like inclusions in transfected cells, in the absence of infection or other viral proteins. The results presented herein have also identified several smaller regions of sequence, and even single residues, within this third of μNS that are required for inclusion formation.

An otherwise-uncharacterized region of μNS (residues 41 to 172) affected the shape of the inclusions, causing them to be more compact and less fenestrated when present in the inclusion-forming protein. Without intending to be bound by theory, this effect could reflect a direct interaction of some portion of residues 41 to 172 with the C-terminal, inclusion-forming region of μNS or with some cellular protein, which in an unknown manner produces more compact inclusions. Without intending to be bound by theory, this effect could also reflect an indirect mechanism, such as a reduction in the turnover rate of the inclusion-forming protein such that holes do not develop within the inclusions.

Except for the modulation of inclusion shape described in this study and a predicted coiled-coil segment from residues 518 to 561 (McCutcheon et al. supra), the large central portion of μNS spanning residues 41 to 560 remains without well-characterized activities. Without intending to be bound by theory, this 41-560 region may contain the residues responsible for μNS associations with other reovirus components, including the individual core-surface proteins, λ1, λ2, and σ2 and whole core particles (Broering et al. (2004) *J. Virol.* 78:1882; Broering (2002) *J. Virol.* 76:8285). In fact, these activities are shared by μNS and μNSC, indicating they do not require the N-terminal 40 residues of μNS. Further truncation/deletion will be performed to determine whether each of the individual core-surface proteins, as well as core particles, may associate with μNS/μNSC through a distinct set of residues, like those for μ2 and σNS in the unique N-terminal region of μNS.

Other components with which μNS/μNSC may yet be shown to associate include the reovirus RNA-dependent RNA polymerase λ3, the reovirus outer-capsid proteins, the reovirus RNA molecules, and any possible number of cellular factors. For each of these potential associations, again, further truncation/deletion analyses will be performed to ascertain whether each component may associate with μNS/μNSC through a distinct set of residues in μNS. Without intending to be bound by theory, it appears that μNS is a protein involved in multiple interactions to form the factory matrix and to recruit other components to the factories, with a modular organization of its primary sequence for performing these many distinct activities.

How μNS Forms Factory-Like Inclusions

Without intending to be bound by theory, there are many possible interactions that could be involved in forming the three-dimensional structure that each inclusion likely represents, even before the addition of other viral components as found in the factories in infected cells. For example, μNS-μNS interactions may be all that are required for forming factory-like inclusions. Alternatively, interactions μNS with one or more cellular factor may be necessary, with the cellular factor(s) acting to bridge between μNS monomers or oligomers. Without intending to be bound by theory, the results presented herein indicate that μNS(471-721) must be capable of mediating or instigating all of the necessary interactions for inclusion formation. The smaller regions within μNS(471-721) that are required for forming inclusions might be directly involved in these interactions. The consensus motif that spans residues 563 to 574 of μNS, and that is partially conserved in the homologous proteins of avian orthoreoviruses and aquareoviruses, includes residues His570 and Cys572, which are required for inclusion formation. Without intending to be bound by theory, given that His and Cys residues have strong potential to chelate transition-metal ions such as $Zn^{2+}$, it is thought that metal chelation by His570 and Cys572 is a part of their role in forming inclusions. Moreover, considering that His570 and Cys572 are so closely spaced and that nearby residues with the same potential for metal chelation—Cys561, His569, and His576—are dispensable for inclusion formation, it is thought, without intending to be bound by theory, that His 570 and Cys572 form half of an intermolecular metal-chelating motif, similar to the zinc hook of Rad50 (Hopfner et al. (2002) *Nature* 418:562) or the zinc clasp of CD4/8 and Lck (Huse et al. (1998) *J. Biol. Chem.* 273:18729; Kim et al. (2003) *Science* 301:1725). The latter two motifs provide four zinc-chelating residues, two from each participating subunit, and contribute to homodimerization in the case of Rad50 or heterodimerization in the case of CD4/8 and Lck.

Some portion of the C-terminal eight residues of μNS (Phe-Ser-Val-Pro-Thr-Asp-Glu-Leu) (SEQ ID NO:28) is also required for inclusion formation. Since this region contains no His or Cys residues, it must contribute to forming inclusions by a mechanism distinct from that for His570 and Cys572. Although this region is not highly conserved in the homologous proteins of avian orthoreoviruses and aquareoviruses, each of the μNS homologs terminates in Leu and has at least one acidic residue and no basic residues in its C-terminal eight positions.

Evidence presented herein indicates that the more N-terminal of the predicted coiled-coil segments in μNS (McCutcheon et al., supra) is required for inclusion formation, but that the loss of function resulting from its deletion can be largely rescued by fusion to GFP. Without intending to be bound by theory, this indicates that the role of the first predicted coiled-coil segment is in self-association, which GFP can also mediate (Campbell supra). Without intending to be bound by theory, although the more C-terminal one of the two predicted coiled-coil segments in μNS has not been directly tested for its role in inclusion formation, it is expected that at least part of it is also required. Coiled-coil interactions between μNS subunits could, for example, mediate formation of basal oligomers, which then interact through other motifs to form the inclusions. Alternatively, one or both of the coiled-coil segments could mediate hetero-oligomerization with a cellular protein. As noted herein, predicted coiled-coil segments are also found flanking the proposed metal-chelation sequences in each of the μNS homologs from avian orthoreoviruses and aquareoviruses, indicating a conserved function for these motifs.

Formation of μNS Inclusions as a Tool to Study Protein-Protein Associations Inside Cells The results presented herein provide evidence that GFP/μNS(471-721) provides a useful platform for examining possible associations between any two proteins in transfected cells. In particular, full-length proteins or protein regions expressed as fusions to GFP/μNS(471-721) should localize to the distinctive, globular inclusions induced by the 471-721 region. The capacity of this fused protein or protein region to associate with another, "test" protein can then be assayed by examining cells in which the test protein has been coexpressed with the inclusion-forming fusion protein. If the test protein localizes to the globular inclusions, then it and the fused protein or protein region can be concluded to associate. Non-fused GFP/μNS(471-721) will be tested in parallel as a negative control for the specificity of test-protein localization to the inclusions. A range of relative expression levels of the two proteins can also be tested, in case relative over-expression of the test protein may retard inclusion formation by the other. We are currently extending our studies of the feasibility of this approach as a general one for studying protein-protein associations within the "native" cellular environment in which the proteins normally reside and function.

Formation of μNS Inclusions as a Tool to Study Protein-Nucleic Acid Associations Inside Cells A further application of this technology is in the identification of nucleotide (e.g., RNA and/or DNA) interactions with proteins. Protein-nucleic acid interactions will be determined by fusing DNA or RNA binding proteins which bind specific nucleotide sequences with, for example, GFP-μNS (471-721), which will localize these proteins to inclusion structures (FIGS. 14A-B). Test RNA or DNA binding sequences will then be cloned on a second plasmid which also contains the specific RNA or DNA sequence bound by the protein fused in frame with GFP-μNS(471-721). This will localize the test or "bait" sequence to inclusion structures. A third plasmid which expresses the protein that is being tested for its ability to bind a particular RNA or DNA sequence is coexpressed in the cell with the other two plasmids. If this protein binds the test or bait sequence, it will colocalize with GFP-μNS(471-721) as a result of its interaction with the sequence. An example of a DNA binding proteins with known specific binding sequence is Gal4. An example of an RNA-binding protein with a known specific binding sequence is MS2.

EXAMPLE VIII

Materials and Methods

Cells and Antibodies

CV-1 cells were maintained in Dulbecco's modified Eagle's medium (Invitrogen Life Technologies) containing 10% fetal bovine serum (HyClone Laboratories) and 10 μg per ml gentamicin solution (Invitrogen Life Technologies). Goat anti-mouse immunoglobulin G (IgG) and goat anti-rabbit IgG conjugated to Alexa 488 or Alexa 594 were obtained from Molecular Probes Inc. (Eugene, Oreg.). Rabbit polyclonal antisera against μNS or μ2 have been described previously (Broering et al. (2000) *J. Virol.* 74:5516; Broering (2002) *J. Virol.* 76:8285; Parker et al. supra). For some experiments, protein A-purified rabbit anti-μNS or anti-μ2 IgG conjugated to Texas Red, Oregon Green, Alexa 488, or Alexa 594 provided in kits (Molecular Probes Inc., Eugene, Oreg.) was used. Mouse monoclonal antibody (MAb) FK2 against conjugated ubiquitin (Fujimuro et al. (1994) *FEBS Letts.* 349: 173) was purchased from Medical & Biological Laboratories. Mouse MAb JL8 against *Aequorea victoria* green fluorescent protein (GFP) was purchased from BD Biosciences. Mouse MAb HA.11 against an immunodominant epitope of influenza A virus hemagglutinin (HA) was purchased from Covance Inc. (Princeton, N.J.). Mouse MAb 3E10 specific for reovirus σNS protein is described in Becker et al. (2001) *J. Virol.* 75:1459. All antibodies were titrated to optimize signal-to-noise ratios.

Expression Constructs

Reovirus proteins were expressed from genes cloned into the mammalian expression vector pCI-neo (Promega). pCI-M3(T1L) and pCI-M3(T3D) to express μNS from type 1 Lang (T1L) or type 3 Dearing (T3D) reovirus have been described previously (Broering (2002) *J. Virol.* 76:8285), as have pCI-M3(41-721) to express μNS residues 41 to 721, Id., pCI-M1(T1L) to express μ2 (Parker et al. supra), and pCI-S3 (T1L) to express σNS (Miller et al. (2003) *J. Virol.* 77:4566). Vent polymerase, which was used for all PCR reactions, and other enzymes were from New England Biolabs unless otherwise stated.

To express μNS residues 1 to 683, site-directed mutagenesis was used to introduce a stop codon at nucleotides 2068 to 2070, followed by a Bsu36I site. QUICKCHANGE™ site-directed mutagenesis (Stratagene, La Jolla, Calif.) was used according to the manufacturer's protocol with pFastBac-M3 (T1L) (Broering et al. (2000) *J. Virol.* 74:5516) as template, forward primer 5'-GGATACGATGAACTAAC CTCAGGCTAAATCATTGCG-3' (SEQ ID NO:29), and reverse primer 5'-CGCAATGATTTAGCCTGAG GTTAGTTCATCGTATCC-3' (SEQ ID NO:30) (bold, nucleotide change to add the stop codon; single underline, nucleotide change to add the restriction site). The region containing the desired mutations was excised by digestion with HindIII and then ligated to pFastBac-M3(T1L) that had been cut with HindIII to remove the same region, generating pFastBac-M3 (1-683). The subcloned region was sequenced to confirm its correctness. The M3 gene was removed from pFastBac-M3 (1-683) by digestion with SalI and NheI and then ligated to pCI-neo that had been cut with the same enzymes, generating pCI-M3(1-683).

To generate other μNS truncations, start and stop codons and restriction sites were introduced at different positions in the M3 gene by PCR amplification of the desired M3 region. The truncations were made in either T1L or T3D M3. We have found no difference in inclusion formation with T1L and T3D μNS (Broering (2002) *J. Virol.* 76:8285; Miller et al. (2003) *J. Virol.* 77:4566), suggesting that the truncations from these allelic μNS proteins are directly comparable. Additionally, the T1L and T3D μNS proteins are ~96% identical (McCutcheon et al. (1999) *Virology.* 264:16). Each PCR reaction was performed with pGEM-4Z-M3(T1L) or pGEM-4Z-M3 (T3D) (Broering et al. (2000) *J. Virol.* 74:5516) as template and the primers listed in Table 3. Each PCR product was cut with the restriction enzymes listed in Table 3 and then ligated to a plasmid that had been cut with these same enzymes, the plasmid being either pGEM-4Z (for pGEM-4Z-M3(1-173) and pGEM-4Z-M3(1-221)) or the template plasmid (for all other constructs). The correct nucleic acid sequence of each construct was confirmed by sequencing. The truncated M3 genes were subcloned into pCI-neo by using the restriction enzymes listed in Table 1. Each construct was named for the residues of µNS that the expressed protein should ultimately contain (Tables 1 and 3).

TABLE 3

| Construct | Primer 1 | Primer 2 | Enzymes |
|---|---|---|---|
| pGEM-4Z-M3 (1-713) | CGGGATCCTCGAGCTAATCAA TCAGGTCAGCAGCGCCGTCG (SEQ ID NO: 31) | 1021-1040 | BstEII, BamHI |
| pGEM-4Z-M3 (1-700) | CGGGATCCTCGAGCTAAGTGG CTGATAGAAGGGAGGG (SEQ ID NO: 32) | 1021-1040 | BstEII, BamHI |
| pGEM-4Z-M3 (1-470) | GGGGTACCTATCGTTCTAGAA AGAGCACCT (SEQ ID NO: 33) | 778-796 | AvaI, KpnI |
| pGEM-4Z-M3 (1-362) | GGGGTACCTAAGAAGTAATGG AAATCACTTGCG (SEQ ID NO: 34) | T7 promoter | StyI, KpnI |
| pGEM-4Z-M3 (1-221) | GGGGTACCTAATCATGAGTTG TCTGAATATCAGCAGCC (SEQ ID NO: 35) | T7 promoter | BamHI, KpnI |
| pGEM-4Z-M3 (1-173) | GGGGTACCTAGGTTGAAGCAA GCCTCTCG (SEQ ID NO: 36) | T7 promoter | BamHI, KpnI |
| pGEM-4Z-M3 (173-721) | CGGGATCCGTCATGGCTACC AGCGTGTCCGTCAGGAC (SEQ ID NO: 37) | reverse 1513-1533 | AvaI, BamHI |
| pGEM-4Z-M3 (221-721) | CGGGATCCGTCATGGCTGAT GTCCATTTGGCACCAGG (SEQ ID NO: 38) | reverse 1513-1533 | AvaI, BamHI |
| pGEM-4Z-M3 (363-721) | CGGGATCCGTCATGGCTGCTT TAAAGTGGGTGG (SEQ ID NO: 39) | reverse 1717-1735 | BsmI, BamHI |
| pGEM-4Z-M3 (471-721) | CGGGATCCGTCATGGCTTCCA ATGACGTGACAGATGG (SEQ ID NO: 40) | reverse 2191-2209 | BsmI, BamHI |

In Table 3 above, each construct was designed to contain the portion of the M3 gene encoding the indicated amino-acid residues of µNS. Primers were written 5' to 3'. For each C-terminal truncation construct, primer 1 is in the reverse orientation relative to the coding strand, and the added stop codon is bolded. For each N-terminal truncation construct, primer 1 is in the forward orientation relative to the coding strand, and the added start-codon cassette is bolded. The BamHI or KpnI restriction enzyme site added near the 5' end of each primer is underlined; for the 1-470, 1-362, 1-221, and 1-173 constructs, the restriction site overlaps the stop codon by one nucleotide. Primer 2 for each PCR reaction comprised the indicated nucleotides in the M3 gene plus strand, the eighteen nucleotides in the T7 promoter of pGEM-4Z, or the reverse complement of the indicated nucleotides in the M3 gene plus strand. Each PCR product was digested with the indicated enzymes for cloning.

The pEGFP-N1 and pEGFP-C1 vectors (BD Biosciences, Franklin Lakes, N.J.) were respectively used to express fusions of enhanced *A. victoria* GFP to the C- or N-terminus of the desired µNS region. pEGFP-N1-M3(T1L) was previously constructed to express GFP fused to the C terminus of µNS (µNS/GFP) (Broering (2002) *J. Virol.* 76:8285). To express GFP fused to the N-terminus of µNS residues 471 to 721, pGEM-4Z-M3(471-721) was cut with SalI and KpnI, and the excised fragment was ligated to pEGFP-C1 that had been cut with the same enzymes, generating pEGFP-C1-M3 (471-721). To express GFP fused to the N-termini of even smaller C-terminal regions of µNS, an EcoRI site was introduced at the desired position in the M3 gene during PCR amplification. Each PCR reaction was performed with pGEM-4Z-M3(T1L) (Broering et al. (2000) *J. Virol.* 74:5516) as template, the forward primers listed in Table 2, and a reverse primer complementary to the 3' end of the M3 coding strand with an added BamHI site (underlined) (5'-GCAGG GGATCCGATGAATGGGGGTCGGGAAGGCTTAA GGG-3') (SEQ ID NO:41). Each PCR product was cut with EcoRI and BamHI and was then ligated to pEGFP-C1 that had been cut with the same enzymes. The correct nucleic acid sequence of each construct was confirmed by sequencing, and the construct was named for the residues of µNS that the expressed protein contains (Table 2).

To generate HA-tagged fusions, epitope-encoding forward primer 5'-CGTAGCTAGCGTCATGGCTTACCCATACGA CGTCCCAGACTACGCTCTCGAGATG (SEQ ID NO:42) and reverse primer 5'-GCATCTCGAGAGCGTAGTCTGGG ACGTCGTATGGGTAAGCCATGACGCTAGCTACG-3' (SEQ ID NO:43) (underlines indicate NheI and XhoI sites added to each) were annealed by boiling in 1×SSC (150 mM NaCl, 15 mM sodium citrate, pH 7.0) followed by cooling at room temperature for 1 hour. The duplex oligonucleotide and vector pCI-neo were then digested with NheI and XhoI, and the products were ligated to generate pCI-neo-HA. The region encoding µNS(561-721) was amplified by PCR from the template pCI-M3(T1L), using forward primer 5'-GCTA GAATTCATGTAGTCTGGATATG TATTTGAGACAC-CAC-3' (SEQ ID NO:44) and reverse primer 5'-GATCGAT CCCGGGTCGGG AAGGCTTAAGGGATTAGGGCAA-3' (SEQ ID NO:45) (underlines indicate an EcoRI or SmaI site added to each). The PCR product and vector pCI-neo-HA were then sequentially digested with SmaI and EcoRI, and the products were ligated to generate pCI-neo-HA-M3(561-721). The region encoding µNS(471-721) was amplified by PCR from the template pCI-M3(T1L), using forward primer 5'-AGCTCTCGAGGTCATGTCCAGTGACATGGTAGA CGGGATTAAAC-3' (SEQ ID NO:46) (underline indicates an added XhoI site) and reverse primer 5'-CGAAGCAT TAACCCTCAC-3' (SEQ ID NO:47). The PCR product and vector pCI-neo-HA were then digested with XhoI and NotI, and the products were ligated to generate pCI-neo-HA-M3 (471-721). To generate untagged µNS(561-721), PCR was performed using the template pCI-M3(T1L), forward primer 5'-AGCTGAATTCGTCATGGCTT GTAGTCTGGTATG-TATTTGAGACAC-3' (SEQ ID NO:48) (underline indicates an added EcoRI site), and reverse primer 5'-CGAAGCAT-TAACCCTCAC-3' (SEQ ID NO:49). The PCR product and vector pCI-neo were then digested with EcoRI and NotI, and the products were ligated to generate pCI-neo-M3(561-721). The correct nucleic acid sequence of the final constructs was confirmed by sequencing.

To generate a µNS(471-721) or full-length µNS protein with residues His569 and His570 changed to glutamine and Cys572 changed to serine, QUICKCHANGE™ site-directed mutagenesis was used following the manufacturer's protocol with pCI-M3(471-721) or pCI-M3(T3D) as template, forward primer 5'-GGATATGTATCTG CGACAACAAACTTCCATTAATGGTCATGC-3' (SEQ ID NO:50), and reverse primer 5'-GCATGACCATTAATG-GAAGTTTGTTGTCGCAGATACA TATCC-3' (SEQ ID NO:51) (bold, nucleotide changes to provide amino acid changes; single underline, nucleotide change to remove a DdeI site for screening purposes). Following the QUICK-CHANGE™ protocol, the mutated pCI-M3(471-721) or pCI-M3(T3D) plasmid was prepared for subcloning by cutting with NheI and EcoRI or BlpI and NotI, respectively. The respectively excised fragment was then ligated to pCI-neo or pCI-M3(T3D) that had been cut with the same respective pair of enzymes, generating the final versions of pCI-M3(471-721)QQS and pCI-M3(T3D)QQS. The correct nucleic acid sequence of these constructs was confirmed by sequencing. To generate a full-length µNS protein with Cys561 or Cys572 changed to Ser or His569, His570, or His576 changed to Gln, QUICKCHANGE™ site-directed mutagenesis was used following the manufacturer's protocol with pCI-M3(T3D) as template and the primers listed in Table 4. Following the QUICKCHANGE™ protocol, each mutated plasmid was prepared for subcloning by cutting with BlpI and NotI. In each case, the excised fragment was then ligated to pCI-M3 (T3D) that had been cut with the same enzymes, generating the constructs as named in Table 4. The correct nucleic acid sequence of each subcloned region was confirmed by sequencing. To generate a fusion of µNS residues 1 to 41 to the N terminus of GFP and µNS residues 471 to 721 to the C terminus of GFP, DNA encoding residues 1 to 41 of µNS and a large portion of GFP was removed from pEGFP-N1-M3(1-41), Id., by digestion with NheI and BsrGI. pEGFP-C1-M3 (471-721) was also cut with these enzymes, and the two DNA fragments were ligated to generate pEGFP-M3(1-41)/GFP/M3(471-721). To generate a fusion of µNS residues 1 to 12 to the N terminus of GFP and µNS residues 471 to 721 to the C terminus of GFP, forward primer 5'-AATTCATGGCTTCATTCAAGGGATTCTCCGTCAACA CTGTTG CG-3' (SEQ ID NO:52), and reverse primer 5'-GATCCGCAACAGTGTT GACGGAGAATCCCTTGAAT-GAAGCCATG-3' (SEQ ID NO:53) were annealed to generate a small duplex encoding µNS residues 1 to 12 and having BamHI and EcoRI overhangs at the respective ends (underlined). This small duplex and plasmid pEGFP-N1 were both digested with BamHI and EcoRI and then ligated to yield pEGFP-N1-M3(1-12). This plasmid was then digested with NheI and BsrGI, and the excised fragment was ligated to pEGFP-C1-M3 (471-721) that had been digested with the same enzymes, generating plasmid pEGFP-M3(1-12)/GFP/M3(471-721). The correct nucleic acid sequence of the resulting construct was confirmed by sequencing.

The amino acid sequence of µNS 471 to 721 is as follows:
SNDVTDGIKLQ LDASRQCHECPVLQQKVVELEKQI-IMQKSIQSDPTPVALQPLLSQLRELSSEVTRL
QMELSRAQSLNAQLEADVKSAQSCSLD-MYLRHHTCINGHAKEDE LLDAVVAPDVRRE-IMEKRSEVRQGWCERISKEAAAKC-QTVIDDLTLMNGKQAQ
EITELRDSAEKYEKQIAELVSTITQNQI-TYQQELQALVAKNVELDAL NQRQAKSLRITPSLL-SATPIDSVDDVADLIDFSVPTDEL (SEQ ID NO:1).

TABLE 4

| Mutation | Forward Primer | Reverse Primer |
| --- | --- | --- |
| C561S | CAAGTCAGCTCAATCATCTA GCTTGGATATCTATC (SEQ ID NO: 54) | GATACATATCCAAGCTAGAT GATTGAGCTGACTTG |
| H569Q | GATATGTATCTGCGACAACA CACTTGCATTAATGG (SEQ ID NO: 56) | CCATTAATGCAAGTGTTG TCGCAGATACATATC |
| H570Q | GATATGTATCTGCGACACCA AACTTGCATTAATGG (SEQ ID NO: 58) | CCATTAATGCAAGTTTGGTG TCGCAGATACATATC |
| C572S | GATATGTATCTGCGACACCA CACTTCCATTAATGGTC (SEQ ID NO: 60) | GACCATTAATGGAAGTGTGG TGTCGCAGATACATATC |
| H576Q | CCACACTTGCATCAATGGTC AAGCTAAAGAAGATG (SEQ ID NO: 62) | CATCTTCTTTAGCTTGACCAT TGATGCAAGTGTGG |

In Table 4 above, the desired mutation at the indicated amino-acid position of µNS is identified. Amino-acid residues are written in single-letter code: wild-type residue, position number, mutant residue. The forward primer is written 5' to 3'. In each primer, the nucleotide change to give the desired amino acid change is bold. For the C561S mutant, this change also caused loss of a BfaI restriction enzyme site useful for screening. For the other mutants, an additional nucleotide change was added to cause loss of a restriction enzyme site is single-underlined; the lost site is DdeI for H569Q, H570Q, and C572S and MseI for H576Q.

Transfections and Immunofluorescence Microscopy

Cells were seeded the day before transfection at a density of $1.5 \times 10^4$ per cm$^2$ in 6-well plates (9.6 cm$^2$ per well) containing glass cover slips (19 mm). Cells were transfected with 2 µg of DNA and 7 µl of LIPOFECTAMINE 2000™ (Invitrogen Life Technologies, Carlsbad, Calif.) or 1.5 µl of DNA and 10 µl of POLYFECT® (Qiagen, Valencia, Calif.) according to the manufacturer's directions. Cells were further incubated for 18 to 24 h at 37° C. before fixation for 10 minutes at room temperature in 2% paraformaldehyde in phosphate-buffered saline (PBS) (137 mM NaCl, 3 mM KCl, 8 mM Na$_2$HPO$_4$, 1 mM KH$_2$PO$_4$, pH 7.5) or 3 minutes at −20° C. in ice-cold methanol. Fixed cells were washed three times with PBS, permeabilized, and blocked in PBS containing 1% bovine serum albumin and 0.1% Triton-X100 (PBSAT). Primary antibodies were diluted in PBSAT and incubated with cells for 25 to 40 minutes at room temperature. After three washes in PBS, secondary antibodies diluted in PBSAT were added and incubated with cells for 25 min at room temperature. Cover slips were incubated with 300 nM 4,6-diamidino-2-phenylindole (DAPI) (Molecular Probes Inc., Eugene, Oreg.) in PBS for 5 minutes to counterstain cell nuclei, briefly washed in PBS, and mounted on glass slides with Prolong (Molecular Probes). Samples were examined using a TE-300 inverted microscope (Nikon) equipped with phase and fluorescence optics, and images were collected digitally as described elsewhere (Parker et al. (2002) *J. Virol.* 76:4483). All images were processed and prepared for presentation using Photoshop (Adobe Systems).

Immunoblot Analysis

CV-1 cells were transfected as described for immunofluorescence, and whole cell lysates were collected 18 to 24 hours post transfection (p.t.). CV-1 cells ($1.2 \times 10^6$) were washed briefly in PBS, then scraped into 1 ml of PBS and pelleted. The pelleted cells were resuspended in 30 µl of PBS containing protease inhibitors (Roche Biomedicals, Basel, Switzerland), lysed into sample buffer, boiled for 10 minutes, and subjected to SDS-polyacrylamide gel electrophoresis (SDS-PAGE). Proteins were electroblotted from the gels to nitrocellulose in 25 mM Tris, 192 mM glycine, pH 8.3. Binding of antibodies was detected with alkaline phosphatase-coupled goat anti-mouse IgG (Bio-Rad Laboratories, Hercules, Calif.) and colorimetric reagents p-nitroblue tetrazolium chloride and 5-bromo-4-chloro-3-indolylphosphate p-toluidine salt (Bio-Rad Laboratories, Hercules, Calif.).

Sequence Comparisons

The following µNS and µNS-homolog sequences, each designated as complete coding sequences in GenBank, were compared: µNS of mammalian orthoreoviruses T1L (accession no. AAF13169), type 2 Jones (accession no. AAF13170), and T3D (accession no. AAF13171); µNS of avian orthoreoviruses 1733 (accession no. AAQ81873), S1133 (accession no. AAS78987), 1017-1 (accession no. AAS78988), 2408 (accession no. AAS78990), 601G (accession no. AAS78991), 750505 (accession no. AAS78992), 916SI (accession no. AAS78993), 918 (accession no. AAS78994), 919 (accession no. AAS78995), OS161 (accession no. AAS78996), R2 (accession no. AAS78997), and T6 (accession no. AAS78998); and NS1 of aquareoviruses grass carp 873 (accession no. AAM92735) and golden shiner (accession no. AAM92747). Each sequence is incorporated herein by reference in its entirety for all purposes. Sequences were compared using the Bestfit and Pretty programs from the Genetics Computer Group Wisconsin package. The Multicoil program (website: multicoil.lcs.mit.edu/cgi-bin/multicoil) (Wolf et al. (1997) *Protein Sci.* 6:1179; Mohan et al. (2003) *J. Virol.* 77:12184) was used for predicting coiled-coil regions.

EXAMPLE IX

Rotavirus NSP5

Figure 11:
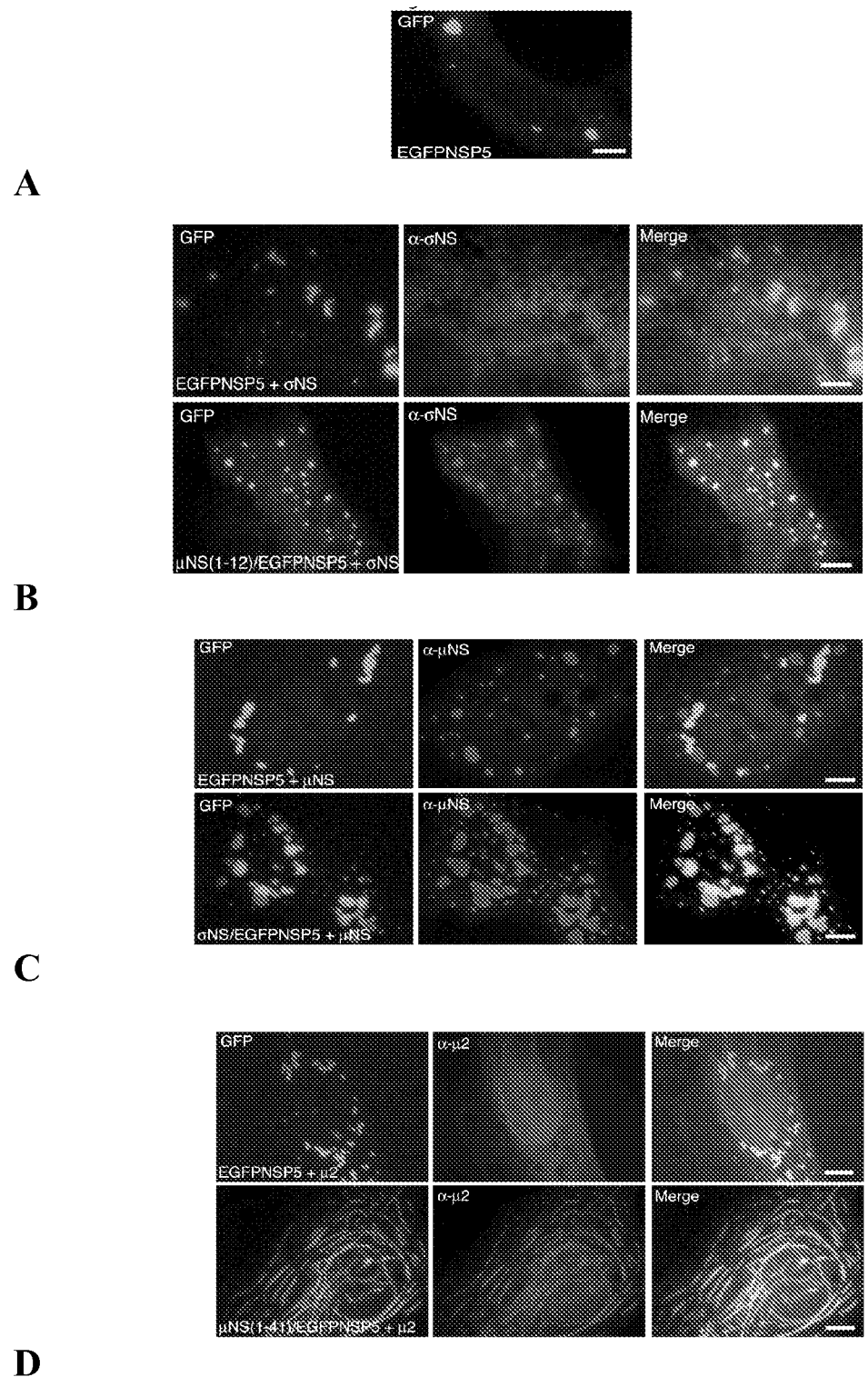
FIGS. 11A-11D depict CV-1 cells transfected with a plasmid encoding enhanced green fluorescent protein (EGFP)-NSP5 (A); co-transfected with EGFP-NSP5 and σNS (B, upper panel) or μNS(1-12)/EGFP-NSP5 and σNS (B, lower panel); co-transfected with EGFP-NSP5 and μNS(C, upper panel) or σNS/EGFP-NSP5 and μNS(C, lower panel); and co-transfected with EGFP-NSP5 and μ2 (D, upper panel) or μNS(1-41)/EGFP-NSP5 and μ2 (D, lower panel).
Figure 12:
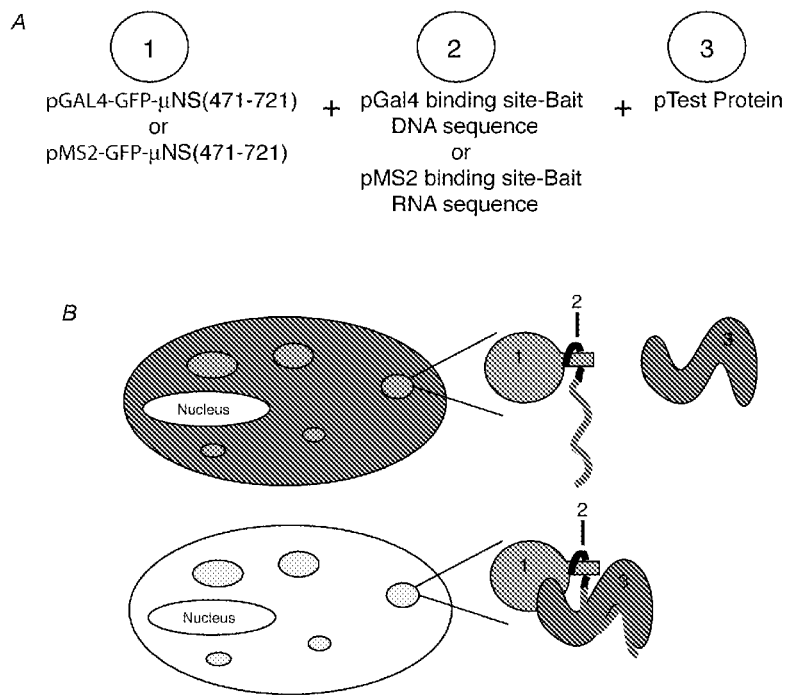
FIGS. 12A-12B depict the detection of protein-nucleic acid interactions. Plasmid constructs expressing a known DNA- (e.g., Gal4) or RNA- (e.g., MS2) binding protein fused to GFP-μNS(471-721) (plasmid 1), the Gal4 DNA-binding site, or MS2 RNA-binding site fused to a bait sequence (plasmid 2), and the protein being tested for its specific nucleic acid binding capability (plasmid 3) (A). Schematic of cells co-transfected with plasmids 1, 2 and 3, in which the test protein does not interact with the inclusion localized sequence (top), and in which the test protein does bind to the inclusion localized sequence, and is localized to inclusions (bottom) (B).

The rotavirus protein NSP5 was examined for its ability to act as a platform for protein-protein interaction studies. NSP5 alone was not able to form inclusion structures, however, when enhanced green fluorescent protein (EGFP) was fused to the N-terminus of NSP5, inclusion structures formed (FIG. 11A). The EGFP-NSP5 fusion protein has been used to identify and examine interactions between reovirus proteins. EGFP-NSP5 was used to examine several interactions (e.g., those discussed above) using either µNS alone, the microtubule associated reovirus µ2 protein, or the EGFP/µNS(471-721) fusion protein.

When coexpressed in cells, µNS and EGFP-NSP5 did not colocalize, and instead formed two distinct populations of inclusion structures (FIG. 11B, top panel). When σNS was fused in frame with EGFP-NSP5 (σNS/EGFP-NSP5) and coexpressed with µNS, the two proteins strongly colocalized (FIG. 11B, bottom panel). By fusing µNS amino-acids 1-12 or 1-41 to the N-terminus of EGFP-NSP5, it was determined that µNS amino-acids 1-12 are sufficient for σNS association, and that µNS amino-acids 1-41 are sufficient for µ2 association. EGFP-NSP5 alone did not associate with either σNS (FIG. 11C, top panel) or µ2 (FIG. 11D, top panel). However, the N-terminal 12 or 41 amino acids of µNS were shown to be sufficient for association with σNS (FIG. 11C, bottom panel) and µ2 (FIG. 11D, bottom panel), respectively, when fused in frame with EGFP-NSP5. EGFP-NSP5 was fused to many different protein fragments of µNS and other proteins to define interaction domains within these proteins. These studies indicate that in addition to GFP/µNS(471-721), inclusion forming proteins such as, for example, EGFP-NSP5 and other inclusion forming proteins from Reoviridae family members, are useful for studying protein-protein interactions in cells.

EXAMPLE X

References

Each of the following is incorporated herein by reference in its entirety for all purposes.
Ali et al. (2001) *Semin. Cancer Biol.* 11:15
Antczak et al. (1992) *Virology* 187:760
Attoui et al. (2002) *J. Gen. Virol.* 83:1941
Becker et al. (2001) *J. Virol.* 75:1459
Becker et al. (2003) *J. Virol.* 77:5948
Broering et al. (2000) *J. Virol.* 74:5516
Broering et al. (2004) *J. Virol.* 78:1882
Broering (2002) *J. Virol.* 76:8285
Broering et al. (2005) *J. Virol.* In Press
Brookes (1993) *J. Gen. Virol.* 74:525
Campbell (2002) *Proc. Natl. Acad. Sci. USA* 99:7877
Collot-Teieira (2004) *Rev. Med. Virol.* 14:301
Dales (1963) *Proc. Natl. Acad. Sci. USA* 50:268
Dales et al. (1965) *Virology* 25:193
Eichwald et al. (2004) *J. Gen. Virol.* 85:625
Fields et al. (1971) *Virology* 43:569
Fujimuro et al. (1994) *FEBS Letts.* 349:173
Gillian et al. (1998) *Virology* 240:1
Gillian et al. (2000) *J. Virol.* 74:5939
Gomatos et al (1981) *J. Virol.* 39:115
Hopfner et al. (2002) *Nature* 418:562
Huismans et al. (1976) *Virology* 70:411
Huse et al. (1998) *J. Biol. Chem.* 273:18729
Kim et al. (2003) *Science* 301:1725
Lee et al (1981) *Virology* 108:134
Mayor (1965) *J. NCI* 35:919
Mbisa et al. (2000) *Virology* 272:16
McCutcheon et al. (1999) *Virology.* 264:16
Miller et al. (2003) *J. Virol.* 77:4566
Miller et al. (2001) *J. Virol.* 75:11664
Mohan et al. (2003) *J. Virol.* 77:12184
Morgan et al. (1975) *Virology* 68:455
Moss, B. (2001) "*Poxyiridae*: the viruses and their replication," 2637-2671. In D. M. Knipe and P. M. Howley (ed.), *Fields Virology*. Lippincott Williams & Wilkins, Philadelphia.
Parker et al. (2002) *J. Virol.* 76:4483
Pipas et al. (2001) *Semin. Cancer Biol.* 11:23
Quimby et al (2001) *Cell. Mol Life Sci.* 58:1766
Restrepo-Hartwig et al. (1996) *J. Virol.* 70:8908
Rhim et al. (1962) *Virology* 17:342
Richardson et al. (1985) *J. Virol.* 56:527
Roizman et al. (2001) "Herpes simplex viruses and their replication," pp. 2231-2295. In D. M. Knipe and P. M. Howley (ed.), *Fields Virology*. Lippincott Williams & Wilkins, Philadelphia.
Schwartz et al. (2002) *Mol. Cell.* 9:505
Sharpe et al. (1982) *Virology* 120:399
Silverstein et al. (1968) *J. Cell Biol.* 36:197
Silverstein et al. (1970) *Virology* 41:564
Silvestri et al. (2004) *J. Virol.* 78:7763
Spendlove et al. (1964) *Cancer Res.* 24:1826
Stamatos et al. (1982) *Proc. Natl. Acad. Sci. USA* 79:3457
Theron et al. (1996) *Arch. Virol.* 141:1143
Touris-Otero et al. (2004) *J. Mol. Biol.* 341:361
Touris-Otero et al. (2004) *Virology* 319:94
Wiener et al. (1989) *Virology* 169:293
Wilson et al. (1984) *Cell* 37:767
Wolf et al. (1997) *Protein Sci.* 6:1179
Zweerink et al. (1971) *Virology* 45:716

EQUIVALENTS

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

What is claimed is:

1. A method for detecting an interaction between a first polypeptide and a second polypeptide comprising:
   providing a cell expressing the first polypeptide being foreign to and operably linked to a viral inclusion body protein or a biologically active portion thereof;
   contacting the first polypeptide with the second polypeptide within the cell;
   allowing formation of an inclusion body; and
   detecting the second polypeptide in the inclusion body if the first polypeptide and the second polypeptide interact.

2. The method of claim 1, wherein the viral inclusion body protein comprises a reoviral protein or a biologically active portion thereof.

3. The method of claim 2, wherein the reoviral protein has an amino acid sequence corresponding to a protein or a biologically active portion of a protein from a reovirus selected from the group consisting of: Orthoreovirus, Orbivirus, Rotavirus, Coltivirus, Seadornavirus, Aquareovirus, Cypovirus, Entomoreovirus, Fijivirus, Phytoreovirus and Orzavirus.

4. The method of claim 3, wherein the reoviral protein has an amino acid sequence corresponding to a protein or a biologically active portion of a protein from Orthoreovirus or Rotavirus.

5. The method of claim 2, wherein the viral inclusion body protein is μNS or NSP5.

6. The method of claim 5, wherein the viral inclusion body protein is a carboxy-terminal one-third of an orthoreoviral μNS protein.

7. The method of claim 1, wherein detecting is by fluorescence microscopy.

8. The method of claim 1, wherein detecting is performed by an automated system.

9. The method of claim 1, wherein the second polypeptide is endogenously expressed by the cell.

10. The method of claim 1, wherein the second polypeptide is expressed by an expression vector.

11. A method for identifying an agent that modulates binding of a first polypeptide to a second polypeptide comprising:
contacting a cell expressing the first polypeptide and the second polypeptide within the cell, wherein the second polypeptide being foreign to and is operably linked to a reoviral inclusion body protein or a biologically active portion thereof
contacting the cell with the agent;
allowing formation of an inclusion body; and
detecting the presence of the first polypeptide in the inclusion body, wherein the presence of the first polypeptide in the inclusion body is altered if the agent modulates binding of the first polypeptide to the second polypeptide.

12. The method of claim 11, wherein the agent is a small molecule.

13. The method of claim 12, wherein the small molecule is selected from a library.

14. The method of claim 11, wherein the agent is a polypeptide.

15. The method of claim 11, wherein the agent increases binding of the first polypeptide to the second polypeptide.

16. The method of claim 11, wherein the agent decreases binding of the first polypeptide to the second polypeptide.

* * * * *

```
                         SEQUENCE LISTING

<160> NUMBER OF SEQ ID NOS: 63

<210> SEQ ID NO 1
<211> LENGTH: 250
<212> TYPE: PRT
<213> ORGANISM: Artificial Sequence
<220> FEATURE:
<223> OTHER INFORMATION: The amino acid sequence of muNS from amino acid
      471 to amino acid 721

<400> SEQUENCE: 1

Ser Asn Asp Val Thr Asp Gly Ile Lys Leu Gln Leu Asp Ala Ser Arg
1               5                   10                  15

Gln Cys His Glu Cys Pro Val Leu Gln Gln Lys Val Val Glu Leu Glu
            20                  25                  30

Lys Gln Ile Ile Met Gln Lys Ser Ile Gln Ser Asp Pro Thr Pro Val
        35                  40                  45

Ala Leu Gln Pro Leu Leu Ser Gln Leu Arg Glu Leu Ser Ser Glu Val
    50                  55                  60

Thr Arg Leu Gln Met Glu Leu Ser Arg Ala Gln Ser Leu Asn Ala Gln
65                  70                  75                  80

Leu Glu Ala Asp Val Lys Ser Ala Gln Ser Cys Ser Leu Asp Met Tyr
                85                  90                  95

Leu Arg His His Thr Cys Ile Asn Gly His Ala Lys Glu Asp Glu Leu
            100                 105                 110

Leu Asp Ala Val Val Ala Pro Asp Val Arg Arg Glu Ile Met Glu Lys
        115                 120                 125

Arg Ser Glu Val Arg Gln Gly Trp Cys Glu Arg Ile Ser Lys Glu Ala
    130                 135                 140

Ala Ala Lys Cys Gln Thr Val Ile Asp Leu Thr Leu Met Asn Gly
145                 150                 155                 160

Lys Gln Ala Gln Glu Ile Thr Glu Leu Arg Asp Ser Ala Glu Lys Tyr
                165                 170                 175

Glu Lys Gln Ile Ala Glu Leu Val Ser Thr Ile Thr Gln Asn Gln Ile
            180                 185                 190

Thr Tyr Gln Gln Glu Leu Gln Ala Leu Val Ala Lys Asn Val Glu Leu
        195                 200                 205

Asp Ala Leu Asn Gln Arg Gln Ala Lys Ser Leu Arg Ile Thr Pro Ser
    210                 215                 220

Leu Leu Ser Ala Thr Pro Ile Asp Ser Val Asp Asp Val Ala Asp Leu
225                 230                 235                 240

Ile Asp Phe Ser Val Pro Thr Asp Glu Leu
                245                 250

<210> SEQ ID NO 2
<211> LENGTH: 10
<212> TYPE: PRT
<213> ORGANISM: Artificial Sequence
<220> FEATURE:
<223> OTHER INFORMATION: c-myc epitope tag sequence

<400> SEQUENCE: 2

Glu Gln Lys Leu Ile Ser Glu Glu Asp Leu
1               5                   10
```

```
<210> SEQ ID NO 3
<211> LENGTH: 9
<212> TYPE: PRT
<213> ORGANISM: Artificial Sequence
<220> FEATURE:
<223> OTHER INFORMATION: HA epitope tag sequence

<400> SEQUENCE: 3

Tyr Pro Tyr Asp Val Pro Asp Tyr Ala
1               5

<210> SEQ ID NO 4
<211> LENGTH: 6
<212> TYPE: PRT
<213> ORGANISM: Artificial Sequence
<220> FEATURE:
<223> OTHER INFORMATION: His-6 epitope tag sequence

<400> SEQUENCE: 4

His His His His His His
1               5

<210> SEQ ID NO 5
<211> LENGTH: 9
<212> TYPE: PRT
<213> ORGANISM: Artificial Sequence
<220> FEATURE:
<223> OTHER INFORMATION: FLAG epitope tag sequence

<400> SEQUENCE: 5

Asp Tyr Lys Asp Asp Asp Asp Lys Cys
1               5

<210> SEQ ID NO 6
<211> LENGTH: 11
<212> TYPE: PRT
<213> ORGANISM: Artificial Sequence
<220> FEATURE:
<223> OTHER INFORMATION: T7 epitope tag sequence

<400> SEQUENCE: 6

Met Ala Ser Met Thr Gly Gly Gln Gln Met Gly
1               5                   10

<210> SEQ ID NO 7
<211> LENGTH: 14
<212> TYPE: PRT
<213> ORGANISM: Artificial Sequence
<220> FEATURE:
<223> OTHER INFORMATION: V5 epitope tag sequence

<400> SEQUENCE: 7

Gly Lys Pro Ile Pro Asn Pro Leu Leu Gly Leu Asp Ser Thr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: VSV-G epitope tag sequence

<400> SEQUENCE: 8

Tyr Thr Asp Ile Glu Met Asn Arg Leu Gly Lys
1               5                   10

<210> SEQ ID NO 9
<211> LENGTH: 5
```

```
<212> TYPE: PRT
<213> ORGANISM: Artificial Sequence
<220> FEATURE:
<223> OTHER INFORMATION: ECS epitope tag sequence

<400> SEQUENCE: 9

Asp Asp Asp Asp Lys
1               5

<210> SEQ ID NO 10
<211> LENGTH: 8
<212> TYPE: PRT
<213> ORGANISM: Artificial Sequence
<220> FEATURE:
<223> OTHER INFORMATION: ECS epitope tag sequence

<400> SEQUENCE: 10

Asp Tyr Lys Asp Asp Asp Asp Lys
1               5

<210> SEQ ID NO 11
<211> LENGTH: 6
<212> TYPE: PRT
<213> ORGANISM: Artificial Sequence
<220> FEATURE:
<223> OTHER INFORMATION: AU1 epitope tag sequence

<400> SEQUENCE: 11

Asp Thr Tyr Arg Tyr Ile
1               5

<210> SEQ ID NO 12
<211> LENGTH: 6
<212> TYPE: PRT
<213> ORGANISM: Artificial Sequence
<220> FEATURE:
<223> OTHER INFORMATION: AU5 epitope tag sequence

<400> SEQUENCE: 12

Thr Asp Phe Tyr Leu Lys
1               5

<210> SEQ ID NO 13
<211> LENGTH: 13
<212> TYPE: PRT
<213> ORGANISM: Artificial Sequence
<220> FEATURE:
<223> OTHER INFORMATION: E-tag epitope tag sequence

<400> SEQUENCE: 13

Gly Ala Pro Val Pro Tyr Pro Asp Pro Leu Glu Pro Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: S-Tag epitope tag sequence

<400> SEQUENCE: 14

Lys Glu Thr Ala Ala Ala Lys Phe Glu Arg Gln His Met Asp Ser
1               5                   10                  15

<210> SEQ ID NO 15
<211> LENGTH: 6
<212> TYPE: PRT
<213> ORGANISM: Artificial Sequence
```

```
<220> FEATURE:
<223> OTHER INFORMATION: Glu-Glu epitope tag sequence

<400> SEQUENCE: 15

Glu Tyr Met Pro Met Glu
1               5

<210> SEQ ID NO 16
<211> LENGTH: 12
<212> TYPE: PRT
<213> ORGANISM: Artificial Sequence
<220> FEATURE:
<223> OTHER INFORMATION: HSV epitope tag sequence

<400> SEQUENCE: 16

Ser Gln Pro Glu Leu Ala Pro Glu Asp Pro Glu Asp
1               5                   10

<210> SEQ ID NO 17
<211> LENGTH: 11
<212> TYPE: PRT
<213> ORGANISM: Artificial Sequence
<220> FEATURE:
<223> OTHER INFORMATION: KT3 epitope tag sequence

<400> SEQUENCE: 17

Lys Pro Pro Thr Pro Pro Pro Glu Pro Glu Thr
1               5                   10

<210> SEQ ID NO 18
<211> LENGTH: 39
<212> TYPE: DNA
<213> ORGANISM: Artificial Sequence
<220> FEATURE:
<223> OTHER INFORMATION: Construction primer sequence

<400> SEQUENCE: 18
cggaattcgt gtagtctgga tatgtatttg agacaccac                      39

<210> SEQ ID NO 19
<211> LENGTH: 34
<212> TYPE: DNA
<213> ORGANISM: Artificial Sequence
<220> FEATURE:
<223> OTHER INFORMATION: Construction primer sequence

<400> SEQUENCE: 19
cggaattcgg aagcggctgc caaatgccaa actg                           34

<210> SEQ ID NO 20
<211> LENGTH: 37
<212> TYPE: DNA
<213> ORGANISM: Artificial Sequence
<220> FEATURE:
<223> OTHER INFORMATION: Construction primer sequence

<400> SEQUENCE: 20
cggaattcga tggacttgac tcagatgaat ggaaagc                        37

<210> SEQ ID NO 21
<211> LENGTH: 36
<212> TYPE: DNA
<213> ORGANISM: Artificial Sequence
<220> FEATURE:
<223> OTHER INFORMATION: Construction primer sequence

<400> SEQUENCE: 21
```

```
cggaattcga tggcctccct tctatcagcc actcct                        36
```

<210> SEQ ID NO 22
<211> LENGTH: 12
<212> TYPE: PRT
<213> ORGANISM: Artificial Sequence
<220> FEATURE:
<223> OTHER INFORMATION: muNS consensus motif
<220> FEATURE:
<221> NAME/KEY: MISC_FEATURE
<222> LOCATION: (1)..(1)
<223> OTHER INFORMATION: X is I or L
<220> FEATURE:
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (6)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is T or V
<220> FEATURE:
<221> NAME/KEY: MISC_FEATURE
<222> LOCATION: (11)..(11)
<223> OTHER INFORMATION: X is I or V

<400> SEQUENCE: 22

Xaa Xaa Xaa Tyr Leu Xaa Xaa His Xaa Cys Xaa Asn
1               5                   10

<210> SEQ ID NO 23
<211> LENGTH: 18
<212> TYPE: PRT
<213> ORGANISM: Artificial Sequence
<220> FEATURE:
<223> OTHER INFORMATION: muNS consensus motif from a mammalian
      orthoreovirus

<400> SEQUENCE: 23

Cys Ser Leu Asp Met Tyr Leu Arg His His Thr Cys Ile Asn Gly His
1               5                   10                  15

Thr Lys

<210> SEQ ID NO 24
<211> LENGTH: 18
<212> TYPE: PRT
<213> ORGANISM: Artificial Sequence
<220> FEATURE:
<223> OTHER INFORMATION: muNS consensus motif from a mammalian
      orthoreovirus

<400> SEQUENCE: 24

Cys Ser Leu Asp Met Tyr Leu Lys His His Thr Cys Ile Asn Ser His
1               5                   10                  15

Val Lys

<210> SEQ ID NO 25
<211> LENGTH: 18
<212> TYPE: PRT
<213> ORGANISM: Artificial Sequence
<220> FEATURE:
<223> OTHER INFORMATION: muNS consensus motif from a mammalian
      orthoreovirus

<400> SEQUENCE: 25

Cys Ser Leu Asp Met Tyr Leu Arg His His Thr Cys Ile Asn Gly His
1               5                   10                  15

```
Ala Lys

<210> SEQ ID NO 26
<211> LENGTH: 18
<212> TYPE: PRT
<213> ORGANISM: Artificial Sequence
<220> FEATURE:
<223> OTHER INFORMATION: muNS consensus motif from avian
      orthoreovirus isolates

<400> SEQUENCE: 26

Asp His Leu Leu Ala Tyr Leu Asn Glu His Val Cys Val Asn Ala Lys
1               5                   10                  15

Asp His

<210> SEQ ID NO 27
<211> LENGTH: 18
<212> TYPE: PRT
<213> ORGANISM: Artificial Sequence
<220> FEATURE:
<223> OTHER INFORMATION: muNS consensus motif from aquareovirus isolates

<400> SEQUENCE: 27

Tyr Ser Ile Gln Gln Tyr Leu His Ser His Thr Cys Val Asn Thr Gln
1               5                   10                  15

Glu Leu

<210> SEQ ID NO 28
<211> LENGTH: 8
<212> TYPE: PRT
<213> ORGANISM: Artificial Sequence
<220> FEATURE:
<223> OTHER INFORMATION: c-terminal eight residues of muNS sequence

<400> SEQUENCE: 28

Phe Ser Val Pro Thr Asp Glu Leu
1               5

<210> SEQ ID NO 29
<211> LENGTH: 36
<212> TYPE: DNA
<213> ORGANISM: Artificial Sequence
<220> FEATURE:
<223> OTHER INFORMATION: Mutagenesis primer

<400> SEQUENCE: 29
ggatacgatg aactaacctc aggctaaatc attgcg                               36

<210> SEQ ID NO 30
<211> LENGTH: 36
<212> TYPE: DNA
<213> ORGANISM: Artificial Sequence
<220> FEATURE:
<223> OTHER INFORMATION: Mutagenesis primer

<400> SEQUENCE: 30
cgcaatgatt tagcctgagg ttagttcatc gtatcc                               36

<210> SEQ ID NO 31
<211> LENGTH: 41
<212> TYPE: DNA
<213> ORGANISM: Artificial Sequence
<220> FEATURE:
<223> OTHER INFORMATION: Mutagenesis primer

<400> SEQUENCE: 31
```

```
cgggatcctc gagctaatca atcaggtcag cagcgccgtc g                           41
```

<210> SEQ ID NO 32
<211> LENGTH: 37
<212> TYPE: DNA
<213> ORGANISM: Artificial Sequence
<220> FEATURE:
<223> OTHER INFORMATION: Mutagenesis primer

<400> SEQUENCE: 32

```
cgggatcctc gagctaagtg gctgatagaa gggaggg                                37
```

<210> SEQ ID NO 33
<211> LENGTH: 30
<212> TYPE: DNA
<213> ORGANISM: Artificial Sequence
<220> FEATURE:
<223> OTHER INFORMATION: Mutagenesis primer

<400> SEQUENCE: 33

```
ggggtaccta tcgttctaga aagagcacct                                        30
```

<210> SEQ ID NO 34
<211> LENGTH: 33
<212> TYPE: DNA
<213> ORGANISM: Artificial Sequence
<220> FEATURE:
<223> OTHER INFORMATION: Mutagenesis primer

<400> SEQUENCE: 34

```
ggggtaccta agaagtaatg gaaatcactt gcg                                    33
```

<210> SEQ ID NO 35
<211> LENGTH: 38
<212> TYPE: DNA
<213> ORGANISM: Artificial Sequence
<220> FEATURE:
<223> OTHER INFORMATION: Mutagenesis primer

<400> SEQUENCE: 35

```
ggggtaccta atcatgagtt gtctgaatat cagcagcc                               38
```

<210> SEQ ID NO 36
<211> LENGTH: 29
<212> TYPE: DNA
<213> ORGANISM: Artificial Sequence
<220> FEATURE:
<223> OTHER INFORMATION: Mutagenesis primer

<400> SEQUENCE: 36

```
ggggtaccta ggttgaagca agcctctcg                                         29
```

<210> SEQ ID NO 37
<211> LENGTH: 37
<212> TYPE: DNA
<213> ORGANISM: Artificial Sequence
<220> FEATURE:
<223> OTHER INFORMATION: Mutagenesis primer

<400> SEQUENCE: 37

```
cgggatccgt catggctacc agcgtgtccg tcaggac                                37
```

<210> SEQ ID NO 38
<211> LENGTH: 37
<212> TYPE: DNA
<213> ORGANISM: Artificial Sequence

```
<220> FEATURE:
<223> OTHER INFORMATION: Mutagenesis primer

<400> SEQUENCE: 38
cgggatccgt catggctgat gtccatttgg caccagg                              37

<210> SEQ ID NO 39
<211> LENGTH: 33
<212> TYPE: DNA
<213> ORGANISM: Artificial Sequence
<220> FEATURE:
<223> OTHER INFORMATION: Mutagenesis primer

<400> SEQUENCE: 39
cgggatccgt catggctgct ttaaagtggg tgg                                  33

<210> SEQ ID NO 40
<211> LENGTH: 37
<212> TYPE: DNA
<213> ORGANISM: Artificial Sequence
<220> FEATURE:
<223> OTHER INFORMATION: Mutagenesis primer

<400> SEQUENCE: 40
cgggatccgt catggcttcc aatgacgtga cagatgg                              37

<210> SEQ ID NO 41
<211> LENGTH: 40
<212> TYPE: DNA
<213> ORGANISM: Artificial Sequence
<220> FEATURE:
<223> OTHER INFORMATION: Mutagenesis primer

<400> SEQUENCE: 41 gcagggatc cgatgaatgg gggtcgggaa ggcttaaggg                             40

<210> SEQ ID NO 42
<211> LENGTH: 56
<212> TYPE: DNA
<213> ORGANISM: Artificial Sequence
<220> FEATURE:
<223> OTHER INFORMATION: Mutagenesis primer

<400> SEQUENCE: 42
cgtagctagc gtcatggctt acccatacga cgtcccagac tacgctctcg agatgc          56

<210> SEQ ID NO 43
<211> LENGTH: 56
<212> TYPE: DNA
<213> ORGANISM: Artificial Sequence
<220> FEATURE:
<223> OTHER INFORMATION: Mutagenesis primer

<400> SEQUENCE: 43
gcatctcgag agcgtagtct gggacgtcgt atgggtaagc catgacgcta gctacg          56

<210> SEQ ID NO 44
<211> LENGTH: 41
<212> TYPE: DNA
<213> ORGANISM: Artificial Sequence
<220> FEATURE:
<223> OTHER INFORMATION: Mutagenesis primer

<400> SEQUENCE: 44
gctagaattc atgtagtctg gatatgtatt tgagacacca c                          41
```

```
<210> SEQ ID NO 45
<211> LENGTH: 40
<212> TYPE: DNA
<213> ORGANISM: Artificial Sequence
<220> FEATURE:
<223> OTHER INFORMATION: Mutagenesis primer

<400> SEQUENCE: 45
gatcgatccc gggtcgggaa ggcttaaggg attagggcaa                           40

<210> SEQ ID NO 46
<211> LENGTH: 44
<212> TYPE: DNA
<213> ORGANISM: Artificial Sequence
<220> FEATURE:
<223> OTHER INFORMATION: Mutagenesis primer

<400> SEQUENCE: 46
agctctcgag gtcatgtcca gtgacatggt agacgggatt aaac                      44

<210> SEQ ID NO 47
<211> LENGTH: 18
<212> TYPE: DNA
<213> ORGANISM: Artificial Sequence
<220> FEATURE:
<223> OTHER INFORMATION: Mutagenesis primer

<400> SEQUENCE: 47
cgaagcatta accctcac                                                   18

<210> SEQ ID NO 48
<211> LENGTH: 45
<212> TYPE: DNA
<213> ORGANISM: Artificial Sequence
<220> FEATURE:
<223> OTHER INFORMATION: Mutagenesis primer

<400> SEQUENCE: 48
agctgaattc gtcatggctt gtagtctggt atgtatttga gacac                     45

<210> SEQ ID NO 49
<211> LENGTH: 18
<212> TYPE: DNA
<213> ORGANISM: Artificial Sequence
<220> FEATURE:
<223> OTHER INFORMATION: Mutagenesis primer

<400> SEQUENCE: 49
cgaagcatta accctcac                                                   18

<210> SEQ ID NO 50
<211> LENGTH: 42
<212> TYPE: DNA
<213> ORGANISM: Artificial Sequence
<220> FEATURE:
<223> OTHER INFORMATION: Mutagenesis primer

<400> SEQUENCE: 50
ggatatgtat ctgcgacaac aaacttccat taatggtcat gc                        42

<210> SEQ ID NO 51
<211> LENGTH: 42
<212> TYPE: DNA
<213> ORGANISM: Artificial Sequence
<220> FEATURE:
<223> OTHER INFORMATION: Mutagenesis primer

<400> SEQUENCE: 51
```
gcatgaccat taatggaagt ttgttgtcgc agatacatat cc                               42

<210> SEQ ID NO 52
<211> LENGTH: 44
<212> TYPE: DNA
<213> ORGANISM: Artificial Sequence
<220> FEATURE:
<223> OTHER INFORMATION: Mutagenesis primer

<400> SEQUENCE: 52
aattcatggc ttcattcaag ggattctccg tcaacactgt tgcg                             44

<210> SEQ ID NO 53
<211> LENGTH: 44
<212> TYPE: DNA
<213> ORGANISM: Artificial Sequence
<220> FEATURE:
<223> OTHER INFORMATION: Mutagenesis primer

<400> SEQUENCE: 53
gatccgcaac agtgttgacg gagaatccct tgaatgaagc catg                             44

<210> SEQ ID NO 54
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 54
caagtcagct caatcatcta gcttggatat ctatc                                      35

<210> SEQ ID NO 55
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 55
gatacatatc caagctagat gattgagctg acttg                                      35

<210> SEQ ID NO 56
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 56
gatatgtatc tgcgacaaca cacttgcatt aatgg                                      35

<210> SEQ ID NO 57
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 57
ccattaatgc aagtgtgttg tcgcagatac atatc                                      35

<210> SEQ ID NO 58
<211> LENGTH: 35
<212> TYPE: DNA
<213> ORGANISM: Artificial Sequence

```
<220> FEATURE:
<223> OTHER INFORMATION: Mutagenesis primer

<400> SEQUENCE: 58
gatatgtatc tgcgacacca aacttgcatt aatgg                               35

<210> SEQ ID NO 59
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 59
ccattaatgc aagtttggtg tcgcagatac atatc                               35

<210> SEQ ID NO 60
<211> LENGTH: 37
<212> TYPE: DNA
<213> ORGANISM: Artificial Sequence
<220> FEATURE:
<223> OTHER INFORMATION: Mutagenesis primer

<400> SEQUENCE: 60
gatatgtatc tgcgacacca cacttccatt aatggtc                             37

<210> SEQ ID NO 61
<211> LENGTH: 37
<212> TYPE: DNA
<213> ORGANISM: Artificial Sequence
<220> FEATURE:
<223> OTHER INFORMATION: Mutagenesis primer

<400> SEQUENCE: 61
gaccattaat ggaagtgtgg tgtcgcagat acatatc                             37

<210> SEQ ID NO 62
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 62
ccacacttgc atcaatggtc aagctaaaga agatg                               35

<210> SEQ ID NO 63
<211> LENGTH: 35
<212> TYPE: DNA
<213> ORGANISM: Artificial Sequence
<220> FEATURE:
<223> OTHER INFORMATION: Mutagenesis primer

<400> SEQUENCE: 63
catcttcttt agcttgacca ttgatgcaag tgtgg                               35
```